United States Patent
Bakos et al.

(10) Patent No.: US 11,766,261 B2
(45) Date of Patent: Sep. 26, 2023

(54) APPARATUS AND METHOD TO APPLY BUTTRESS TO END EFFECTOR OF SURGICAL STAPLER VIA FIXED BASE

(71) Applicant: Cilag GmbH International, Zug (CH)

(72) Inventors: Gregory J. Bakos, Mason, OH (US); Michael J. Vendely, Lebanon, OH (US); Mark S. Zeiner, Mason, OH (US); Heather Strang, West Chester, OH (US); Pamela M. Ridgley, Lebanon, OH (US); Christopher A. Denzinger, Cincinnati, OH (US); Christopher Q. Seow, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/022,186

(22) Filed: Sep. 16, 2020

(65) Prior Publication Data

US 2022/0079592 A1  Mar. 17, 2022

(51) Int. Cl.
*A61B 17/072* (2006.01)
*A61B 17/00* (2006.01)

(52) U.S. Cl.
CPC ... *A61B 17/07292* (2013.01); *A61B 2017/0053* (2013.01); *A61B 2017/00424* (2013.01);
(Continued)

(58) Field of Classification Search
CPC .... A61B 17/07292; A61B 2017/00424; A61B 2017/00477; A61B 2017/0053;
(Continued)

(56) References Cited

U.S. PATENT DOCUMENTS 2,131,093 A  4/1936 Cage
2,467,190 A  10/1945 Cowles et al.
(Continued)

FOREIGN PATENT DOCUMENTS

EP  2 090 248 A2  8/2009
EP  3 072 460 A2  9/2016
(Continued)

OTHER PUBLICATIONS

U.S. Appl. No. 17/022,209, entitled "Apparatus and Method to Apply Buttress to End Effector of Surgical Stapler via Driven Member," filed Sep. 16, 2020.

(Continued)

*Primary Examiner* — Robert F Long
(74) *Attorney, Agent, or Firm* — Frost Brown Todd LLP

(57) ABSTRACT

An apparatus includes a body with a first body portion, a second body portion opposed from the first body portion, and a connecting portion that couples a proximal end of the first body portion with a proximal end of the second body portion. The connecting portion is configured to permit the first and second body portions to move toward and away from one another between a plurality of angular orientations. The first and second body portions define a distally opening angle. A first adjunct element and a second adjunct element are disposed on outwardly facing surfaces of the first and second body portions. The first and second body portions may be fixed in each of the angular orientations and may simultaneously apply the first and second adjunct elements to first and second jaws, respectively, of a surgical stapler end effector.

3 Claims, 22 Drawing Sheets

(52) U.S. Cl.
CPC ............. *A61B 2017/00477* (2013.01); *A61B 2017/07264* (2013.01); *A61B 2017/07271* (2013.01); *A61B 2017/07278* (2013.01); *A61B 2017/07285* (2013.01)

(58) Field of Classification Search
CPC ........... A61B 2017/07264; A61B 2017/07271; A61B 2017/07278; A61B 2017/07285
USPC ........................................... 227/175.1–182.1
See application file for complete search history.

(56) References Cited

U.S. PATENT DOCUMENTS

| | | | |
|---|---|---|---|
| 3,117,757 A | 12/1960 | Sampson | |
| 3,809,094 A * | 5/1974 | Cook | A61B 13/00 600/218 |
| 3,904,033 A * | 9/1975 | Haerr | A61B 17/34 206/349 |
| 4,506,267 A * | 3/1985 | Harmuth | H01Q 17/001 343/846 |
| 4,930,674 A | 6/1990 | Barak | |
| 5,358,510 A * | 10/1994 | Luscombe | A61B 17/0643 606/151 |
| 5,372,868 A * | 12/1994 | Prewo | E04C 2/34 428/120 |
| 5,470,009 A * | 11/1995 | Rodak | A61B 17/072 227/176.1 |
| 5,655,698 A * | 8/1997 | Yoon | A61B 17/07207 227/176.1 |
| 5,697,542 A * | 12/1997 | Knodel | A61B 17/07207 227/175.1 |
| 5,752,965 A | 5/1998 | Francis et al. | |
| 5,769,892 A | 6/1998 | Kingwell | |
| 5,797,931 A * | 8/1998 | Bito | A61B 17/1285 606/127 |
| 5,810,855 A * | 9/1998 | Rayburn | A61B 17/07207 606/220 |
| 5,833,695 A * | 11/1998 | Yoon | A61B 17/07207 606/139 |
| 5,901,895 A * | 5/1999 | Heaton | A61B 17/07207 227/176.1 |
| 5,902,312 A * | 5/1999 | Frater | A61B 17/07207 606/148 |
| 6,019,791 A | 2/2000 | Wood | |
| 6,099,551 A * | 8/2000 | Gabbay | A61B 17/07207 227/176.1 |
| 6,273,897 B1 | 8/2001 | Dalessandro et al. | |
| 6,325,810 B1 * | 12/2001 | Hamilton | A61B 17/07207 227/175.1 |
| 6,592,597 B2 | 7/2003 | Grant et al. | |
| 6,638,285 B2 | 10/2003 | Gabbay | |
| 7,147,138 B2 | 12/2006 | Shelton, IV | |
| 7,377,928 B2 | 5/2008 | Zubik et al. | |
| 7,380,696 B2 | 6/2008 | Shelton, IV et al. | |
| 7,559,937 B2 | 7/2009 | De La Torre et al. | |
| 7,665,646 B2 | 2/2010 | Prommersberger | |
| 7,708,180 B2 | 5/2010 | Murray et al. | |
| 7,845,533 B2 | 12/2010 | Marczyk et al. | |
| 8,052,697 B2 | 11/2011 | Phillips | |
| 8,210,411 B2 | 7/2012 | Yates et al. | |
| 8,317,790 B2 * | 11/2012 | Bell | A61B 17/07292 606/75 |
| 8,348,130 B2 * | 1/2013 | Shah | A61B 17/07207 227/180.1 |
| 8,408,439 B2 | 4/2013 | Huang et al. | |
| 8,453,904 B2 | 6/2013 | Eskaros et al. | |
| 8,453,914 B2 | 6/2013 | Laurent et al. | |
| 8,464,925 B2 | 6/2013 | Hull et al. | |
| 8,864,009 B2 * | 10/2014 | Shelton, IV | A61B 17/00491 227/175.1 |
| 8,920,444 B2 | 12/2014 | Hiles et al. | |
| 9,186,142 B2 | 11/2015 | Fanelli et al. | |
| 9,211,120 B2 | 12/2015 | Scheib et al. | |
| 9,220,501 B2 | 12/2015 | Baxter, III et al. | |
| 9,517,065 B2 | 12/2016 | Simms et al. | |
| 9,622,746 B2 | 4/2017 | Simms et al. | |
| 9,717,497 B2 | 8/2017 | Zerkle et al. | |
| 9,795,379 B2 | 10/2017 | Leimbach et al. | |
| 9,808,248 B2 | 11/2017 | Hoffman | |
| 9,833,238 B2 * | 12/2017 | Baxter, III | A61B 17/30 |
| 9,839,421 B2 | 12/2017 | Zerkle et al. | |
| 9,844,378 B2 | 12/2017 | Casasanta et al. | |
| 9,925,647 B2 * | 3/2018 | Lafond | G01N 1/02 |
| 9,999,408 B2 | 6/2018 | Boudreaux et al. | |
| 10,092,292 B2 | 10/2018 | Boudreaux et al. | |
| 10,166,023 B2 | 1/2019 | Vendely et al. | |
| 10,213,198 B2 | 2/2019 | Aronhalt et al. | |
| 10,349,939 B2 | 7/2019 | Shelton, IV et al. | |
| 10,869,663 B2 | 12/2020 | Shelton, IV et al. | |
| 10,932,779 B2 * | 3/2021 | Vendely | B32B 7/05 |
| 10,959,721 B2 * | 3/2021 | Shelton, IV | A61B 17/07207 |
| 10,993,716 B2 | 5/2021 | Shelton, IV et al. | |
| 11,033,269 B2 | 6/2021 | Vendely et al. | |
| 11,045,196 B2 | 6/2021 | Olson et al. | |
| 11,051,812 B2 | 7/2021 | Hopkins et al. | |
| 11,058,418 B2 | 7/2021 | Shelton, IV et al. | |
| 11,185,327 B2 * | 11/2021 | Harris | A61B 17/3468 |
| 2005/0070929 A1 | 3/2005 | Dalessandro et al. | |
| 2005/0267325 A1 * | 12/2005 | Bouchier | A61B 17/06004 623/23.72 |
| 2006/0173470 A1 * | 8/2006 | Oray | A61B 17/07207 606/151 |
| 2007/0162056 A1 * | 7/2007 | Gerbi | A61B 17/07207 606/153 |
| 2007/0179528 A1 * | 8/2007 | Soltz | A61B 17/07207 606/219 |
| 2007/0246505 A1 * | 10/2007 | Pace-Floridia | A61L 31/044 227/175.1 |
| 2008/0128469 A1 * | 6/2008 | Dalessandro | A61B 17/07207 227/154 |
| 2008/0169329 A1 * | 7/2008 | Shelton | A61B 17/32 227/180.1 |
| 2008/0203134 A1 * | 8/2008 | Shah | A61B 17/07207 227/176.1 |
| 2009/0001122 A1 * | 1/2009 | Prommersberger | A61B 17/072 227/176.1 |
| 2009/0076510 A1 * | 3/2009 | Bell | A61B 17/07292 606/151 |
| 2009/0084825 A1 | 4/2009 | Larson | |
| 2009/0206125 A1 | 8/2009 | Huitema et al. | |
| 2009/0206126 A1 * | 8/2009 | Huitema | A61B 50/30 227/175.1 |
| 2010/0087840 A1 * | 4/2010 | Ebersole | A61B 17/07207 606/151 |
| 2010/0163598 A1 | 7/2010 | Belzer | |
| 2010/0243393 A1 | 9/2010 | Mahu | |
| 2011/0017802 A1 | 1/2011 | Ma et al. | |
| 2011/0087279 A1 * | 4/2011 | Shah | A61B 17/07207 606/219 |
| 2011/0248064 A1 | 10/2011 | Marczyk | |
| 2012/0018487 A1 | 1/2012 | Bettuchi et al. | |
| 2012/0080336 A1 | 4/2012 | Shelton, IV et al. | |
| 2012/0145767 A1 * | 6/2012 | Shah | A61B 17/07207 227/176.1 |
| 2012/0241503 A1 * | 9/2012 | Baxter, III | A61B 17/068 227/176.1 |
| 2012/0265154 A1 | 10/2012 | Criscuolo et al. | |
| 2013/0037596 A1 * | 2/2013 | Bear | A61B 17/07207 227/176.1 |
| 2013/0075447 A1 * | 3/2013 | Weisenburgh, II | A61B 17/00491 227/176.1 |
| 2013/0146642 A1 * | 6/2013 | Shelton, IV | A61B 17/068 227/177.1 |
| 2013/0214030 A1 * | 8/2013 | Aronhalt | A61B 17/0644 227/176.1 |
| 2013/0256378 A1 * | 10/2013 | Schmid | A61B 17/068 227/176.1 |
| 2014/0058194 A1 | 2/2014 | Soletti et al. | |

(56) References Cited

U.S. PATENT DOCUMENTS

| | | | |
|---|---|---|---|
| 2014/0131418 A1* | 5/2014 | Kostrzewski | A61B 17/068 227/176.1 |
| 2014/0131419 A1* | 5/2014 | Bettuchi | A61B 17/07292 227/176.1 |
| 2014/0158741 A1* | 6/2014 | Woodard, Jr. | A61B 17/0401 227/175.1 |
| 2014/0239036 A1 | 8/2014 | Zerkle et al. | |
| 2014/0288386 A1 | 9/2014 | Zand et al. | |
| 2014/0291379 A1* | 10/2014 | Schellin | A61B 17/068 227/176.1 |
| 2015/0041168 A1* | 2/2015 | Dostinov | B25D 17/24 173/90 |
| 2015/0076212 A1 | 3/2015 | Shelton, IV | |
| 2015/0351758 A1* | 12/2015 | Shelton, IV | A61B 17/0644 606/219 |
| 2015/0351761 A1* | 12/2015 | Shelton, IV | A61B 17/07207 606/219 |
| 2016/0287254 A1* | 10/2016 | Baxter, III | A61B 17/0644 |
| 2017/0055980 A1* | 3/2017 | Vendely | A61B 17/07207 |
| 2017/0055982 A1* | 3/2017 | Zeiner | A61B 17/105 |
| 2017/0056016 A1 | 3/2017 | Barton et al. | |
| 2017/0056018 A1* | 3/2017 | Zeiner | A61B 17/34 |
| 2017/0137155 A1 | 5/2017 | Pape | |
| 2017/0281181 A1 | 10/2017 | Matonick et al. | |
| 2017/0303952 A1* | 10/2017 | Nativ | A61B 17/105 |
| 2018/0235617 A1* | 8/2018 | Shelton, IV | A61B 50/20 |
| 2018/0235626 A1* | 8/2018 | Shelton, IV | A61B 17/07292 |
| 2019/0254671 A1* | 8/2019 | Shankarsetty | A61B 17/07292 |
| 2019/0290267 A1 | 9/2019 | Baxter, III et al. | |
| 2019/0321044 A1 | 10/2019 | Franklin, Sr. | |
| 2019/0343520 A1* | 11/2019 | Williams | A61B 17/07207 |
| 2020/0015817 A1* | 1/2020 | Harris | A61B 17/07207 |
| 2020/0205823 A1* | 7/2020 | Vendely | A61B 17/07207 |
| 2020/0205825 A1 | 7/2020 | Vendely et al. | |
| 2020/0261080 A1 | 8/2020 | Bakos et al. | |
| 2020/0281587 A1 | 9/2020 | Schmid et al. | |
| 2020/0405436 A1 | 12/2020 | Shelton, IV et al. | |
| 2021/0077103 A1* | 3/2021 | Harris | A61B 17/064 |
| 2021/0106329 A1* | 4/2021 | Williams | A61B 17/11 |
| 2021/0177411 A1* | 6/2021 | Williams | A61B 90/03 |
| 2022/0079587 A1* | 3/2022 | Zeiner | A61B 17/07292 |

FOREIGN PATENT DOCUMENTS

| | | | |
|---|---|---|---|
| EP | 3 632 342 A2 | 4/2020 | |
| EP | 3 673 831 A2 | 7/2020 | |
| EP | 2644120 B1 * | 6/2022 | A61B 17/00491 |
| FR | 3016793 A1 * | 7/2015 | A61B 17/7064 |
| WO | WO-2015134682 A1 * | 9/2015 | A61B 17/0643 |

OTHER PUBLICATIONS

U.S. Appl. No. 17/022,214, entitled "Apparatus and Method to Apply Buttresses Separately to Jaws of End Effector of Surgical Stapler," filed Sep. 16, 2020.
U.S. Appl. No. 17/022,414, entitled "Apparatus and Method to Close End Effector of Surgical Stapler onto Buttress," filed Sep. 16, 2020.
U.S. Appl. No. 17/022,419, entitled "Apparatus and Method to Detect Full Seating of Buttress Applicator in End Effector of Surgical Stapler," filed Sep. 16, 2020.
U.S. Appl. No. 17/022,442, entitled "Apparatus and Method to Apply Buttress to End Effector of Surgical Stapler with Authentication," filed Sep. 16, 2020.
U.S. Appl. No. 17/022,520, entitled "Method of Applying Buttress to End Effector of Surgical Stapler," filed Sep. 16, 2020.
U.S. Appl. No. 17/022,209.
U.S. Appl. No. 17/022,214.
U.S. Appl. No. 17/022,414.
U.S. Appl. No. 17/022,419.
U.S. Appl. No. 17/022,442; and.
U.S. Appl. No. 17/022,520.
Gore Seamguard Bioabsorbable Staple Line Reinforcement, Configured for Endoscopic Surgical Staplers, Instructions for Use, Jun. 2019, 136 pgs.
International Search Report and Written Opinion dated Nov. 30, 2021 for Application No. PCT/IB2021/058337, 16 pgs.
International Search Report and Written Opinion dated Nov. 29, 2021 for Application No. PCT/IB2021/058165, 14 pgs.
International Search Report and Written Opinion dated Dec. 2, 2021 for Application No. PCT/IB2021/058414, 14 pgs.
International Search Report and Written Opinion dated Nov. 24, 2021 for Application No. PCT/IB2021/058239, 12 pgs.
International Search Report and Written Opinion dated Nov. 30, 2021 for Application No. PCT/IB2021/058396, 14 pgs.
International Search Report and Written Opinion dated Dec. 2, 2021 for Application No. PCT/IB2021/058412, 15 pgs.
International Search Report and Written Opinion dated Nov. 25, 2021 for Application No. PCT/IB2021/058400, 15 pgs.
International Search Report and Written Opinion dated Feb. 16, 2022 for Application No. PCT/IB2021/060163, 15 pgs.

* cited by examiner

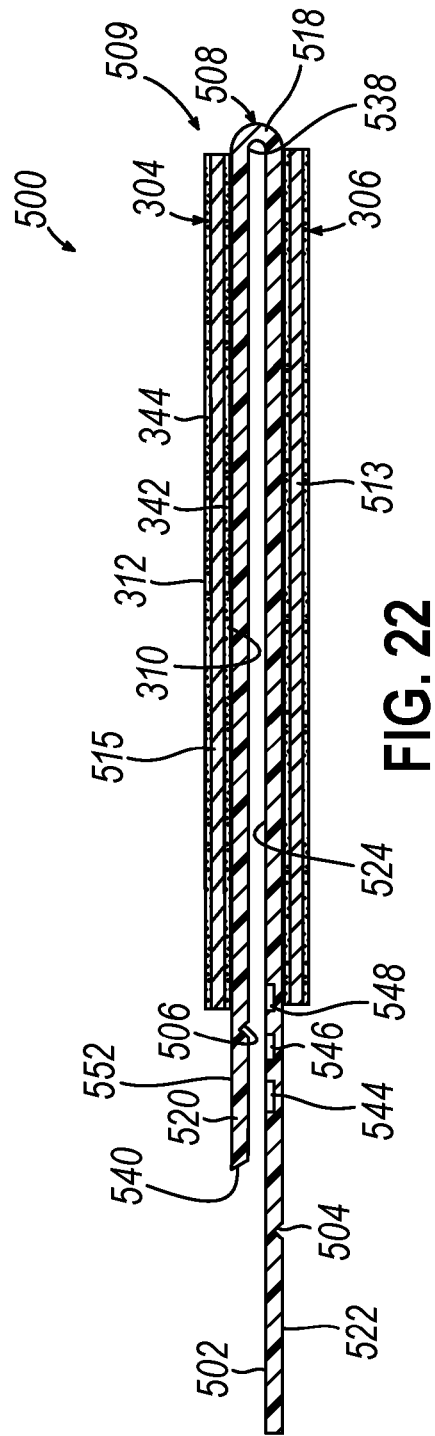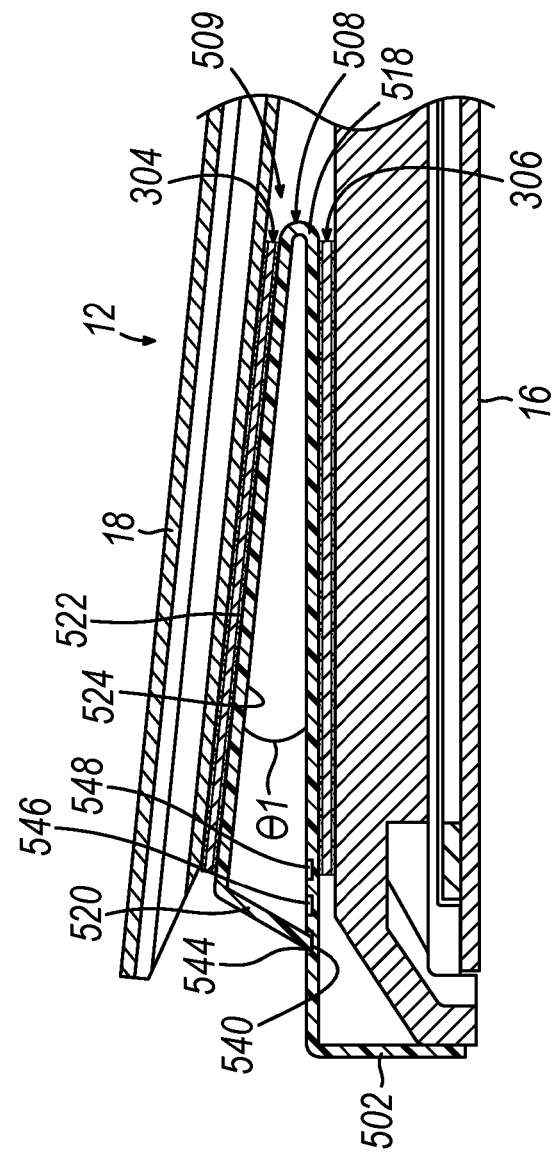

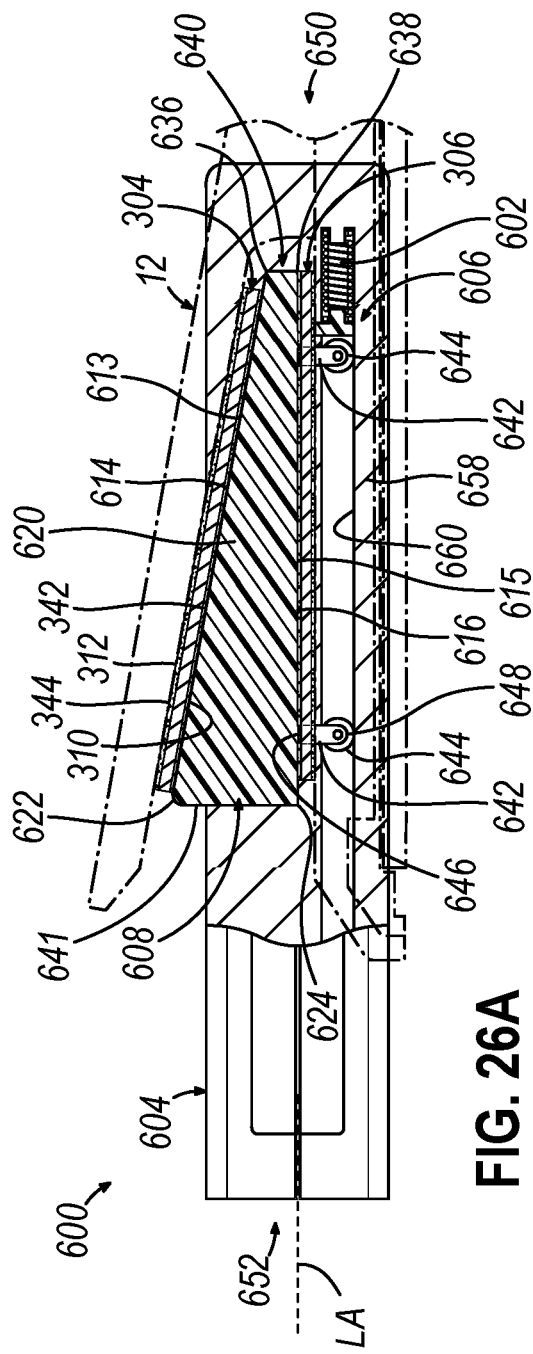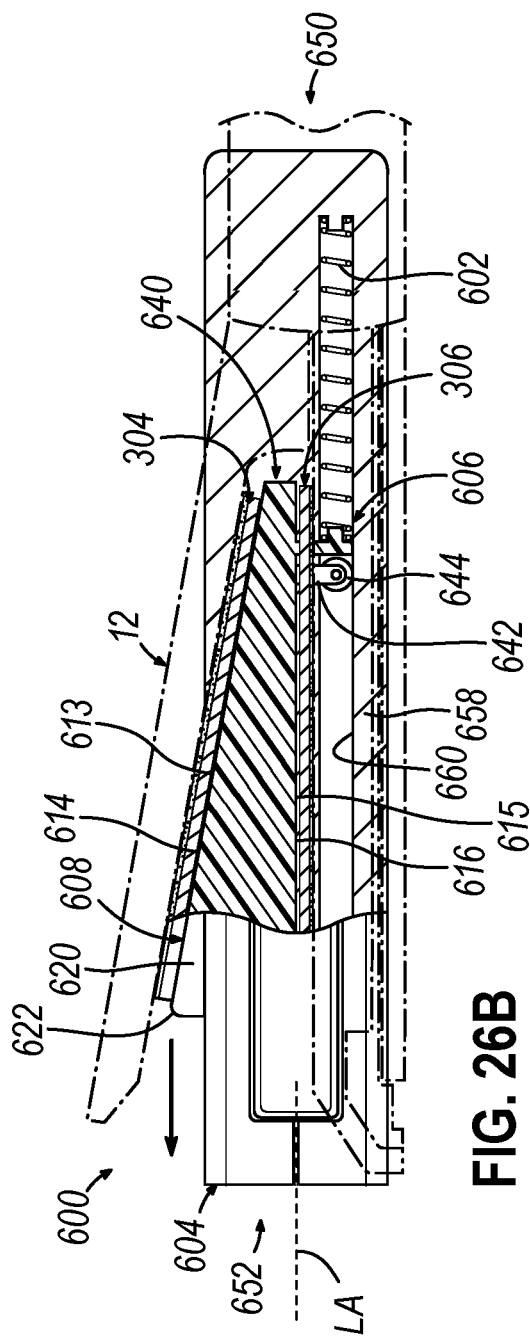

APPARATUS AND METHOD TO APPLY BUTTRESS TO END EFFECTOR OF SURGICAL STAPLER VIA FIXED BASE

BACKGROUND

In some surgical settings, endoscopic surgical instruments may be preferred over traditional open surgical devices in order to make use of a smaller incision in the patient, which may reduce post-operative recovery time and complications. Some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,380,696, entitled "Articulating Surgical Stapling Instrument Incorporating a Two-Piece E-Beam Firing Mechanism," issued Jun. 3, 2008; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents and U.S. Patent Publications is incorporated by reference herein.

Surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 22 depicts a side cross-sectional view of a third exemplary adjunct applicator, showing the applicator in a non-expanded, storage configuration;

FIG. 23 depicts a side cross-sectional view of the end effector of FIG. 3 engaging the adjunct applicator of FIG. 22 while the applicator is in a first expanded, angular configuration;

FIG. 26A depicts a side cross-sectional view of the adjunct applicator of FIG. 25, taken along line 26A-26A of FIG. 25, showing the wedge portion of the applicator in the proximal position engaging the end effector of FIG. 3, shown in phantom; and FIG. 26B depicts a side cross-sectional view of the adjunct applicator cartridge of FIG. 25, showing the wedge portion of the applicator in a distal position engaging the end effector of FIG. 3, shown in phantom.

Figure 1:
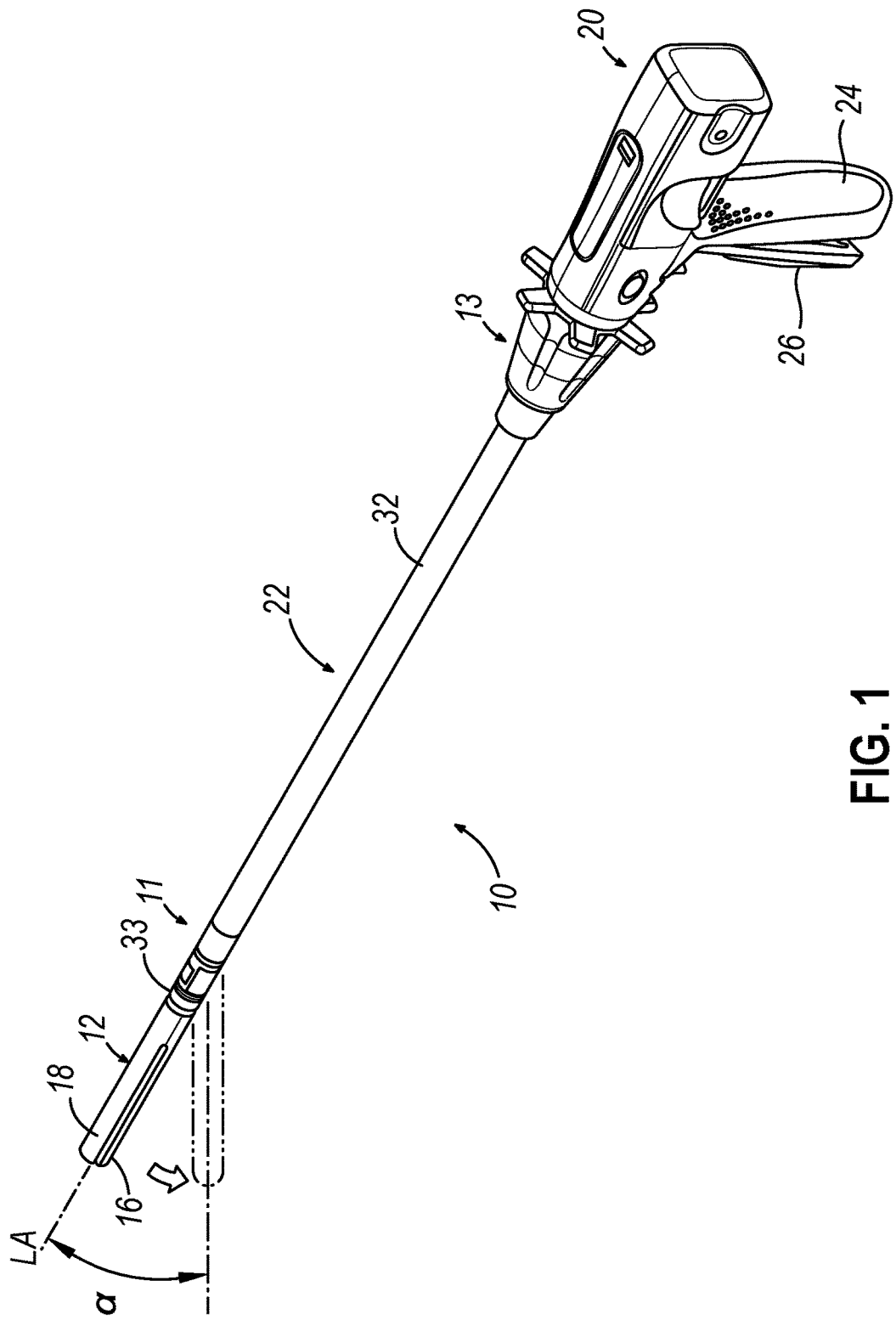
FIG. 1 depicts a perspective view of an exemplary surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

I. Exemplary Surgical Stapler

FIGS. 1-7 depict an exemplary surgical stapling and severing instrument (10) that is sized for insertion through a trocar cannula or an incision (e.g., thoracotomy, etc.) to a surgical site in a patient for performing a surgical procedure. Instrument (10) of the present example includes a handle portion (20) connected to a shaft (22), which distally terminates in an articulation joint (11), which is further coupled with an end effector (12). Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle (a). End effector (12) of the present example includes a lower jaw (16) that includes a staple cartridge (37), and an upper jaw in the form of a pivotable anvil (18).

Handle portion (20) includes a pistol grip (24) and a closure trigger (26). Closure trigger (26) is pivotable toward pistol grip (24) to cause clamping, or closing, of anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to communicate/transmit longitudinal movement from closure tube (32) to closure ring (33).

Figure 2:
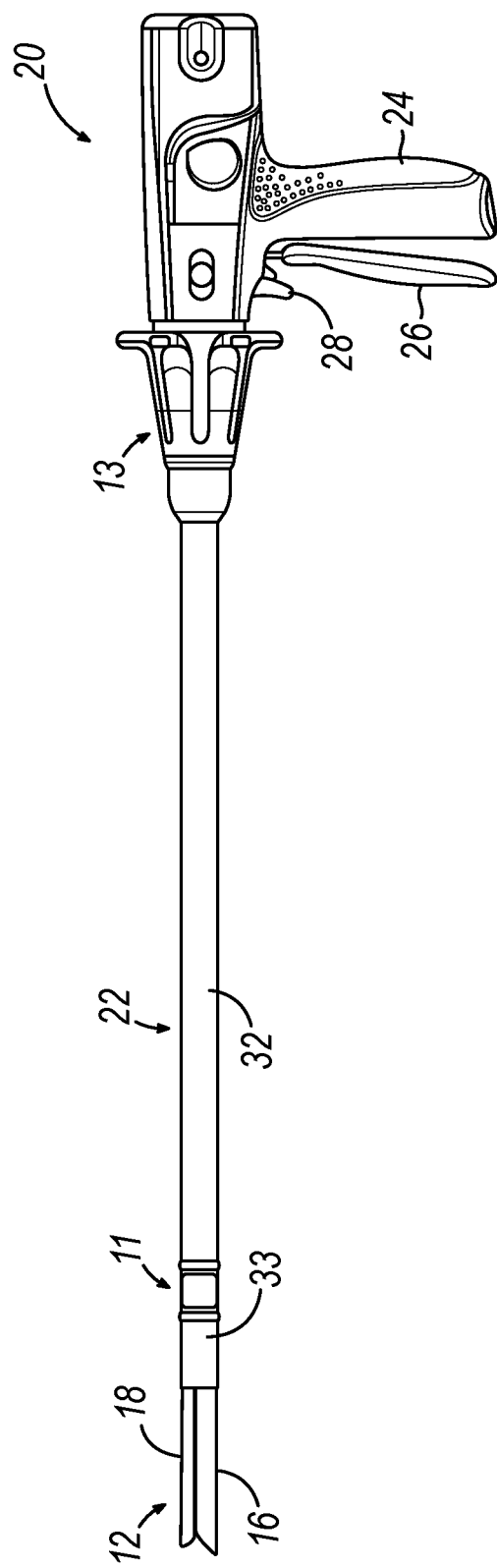
FIG. 2 depicts a side elevational view of the instrument of FIG. 1.

As shown in FIG. 2, handle portion (20) also includes a firing trigger (28). An elongate member (not shown) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below.

As shown in FIGS. 3-6, end effector (12) employs a firing beam (14) that includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44).

Figure 3:
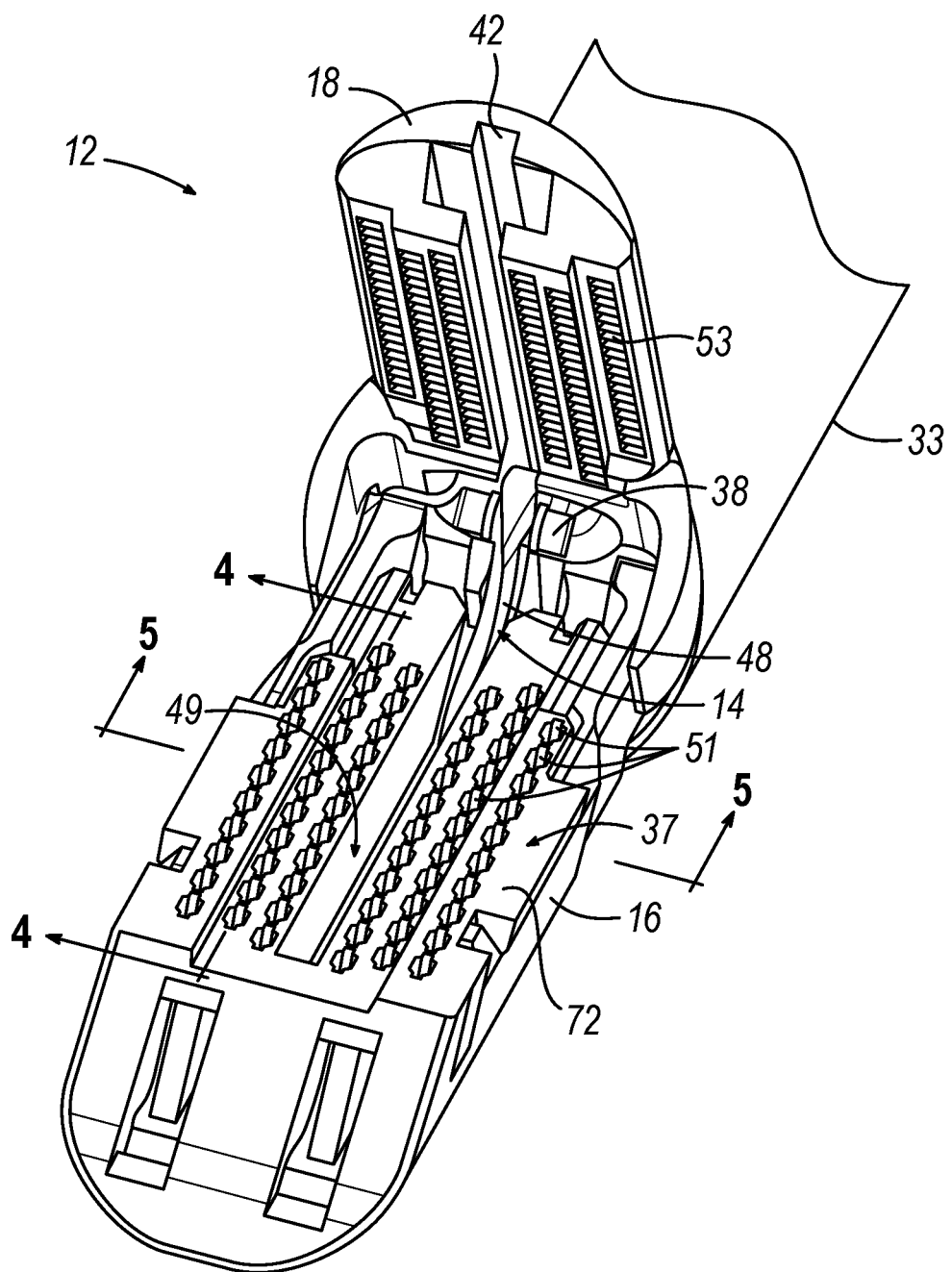
FIG. 3 depicts a perspective view of an end effector of the instrument of FIG. 1 in an open state.
Figure 4A:
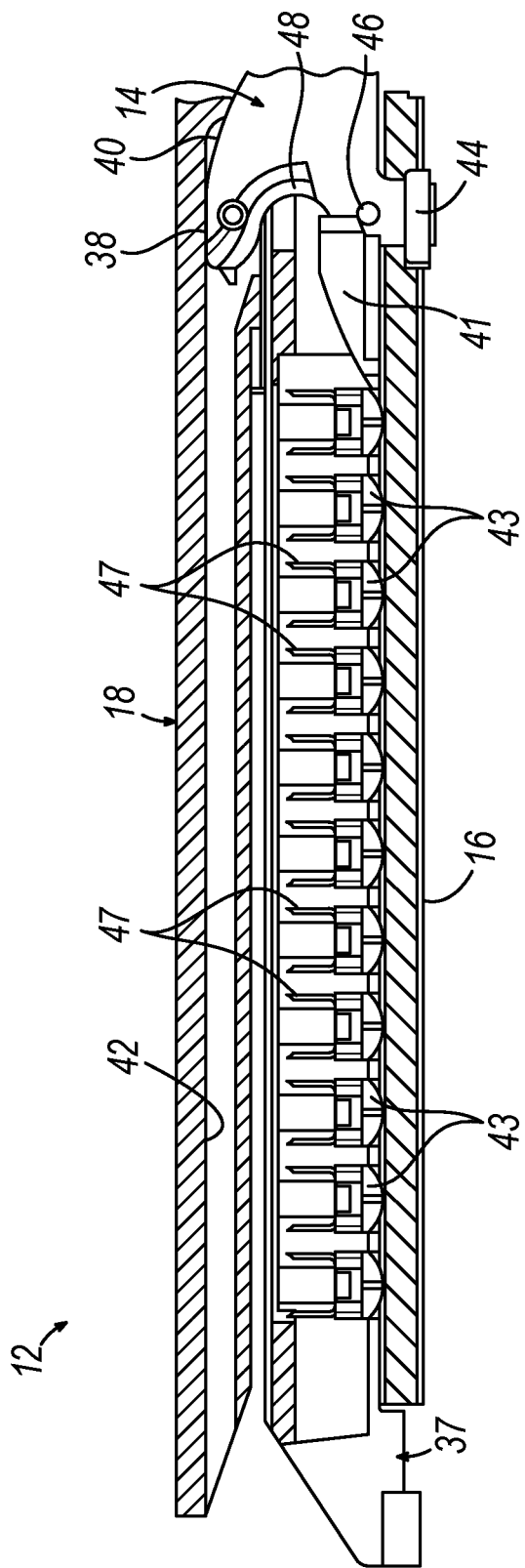
FIG. 4A depicts a side cross-sectional view of the end effector of FIG. 3, taken along line 4-4 of FIG. 3, with a firing beam in a proximal position.
Figure 4B:
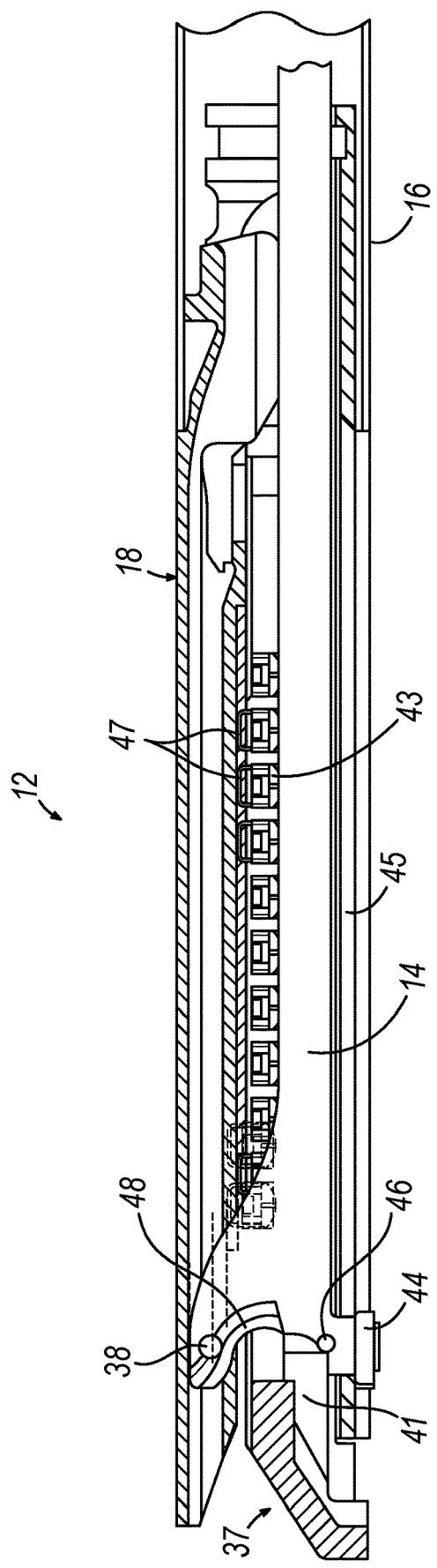
FIG. 4B depicts a side cross-sectional view of the end effector of FIG. 3, taken along line 4-4 of FIG. 3, with the firing beam in a distal position.
Figure 5:
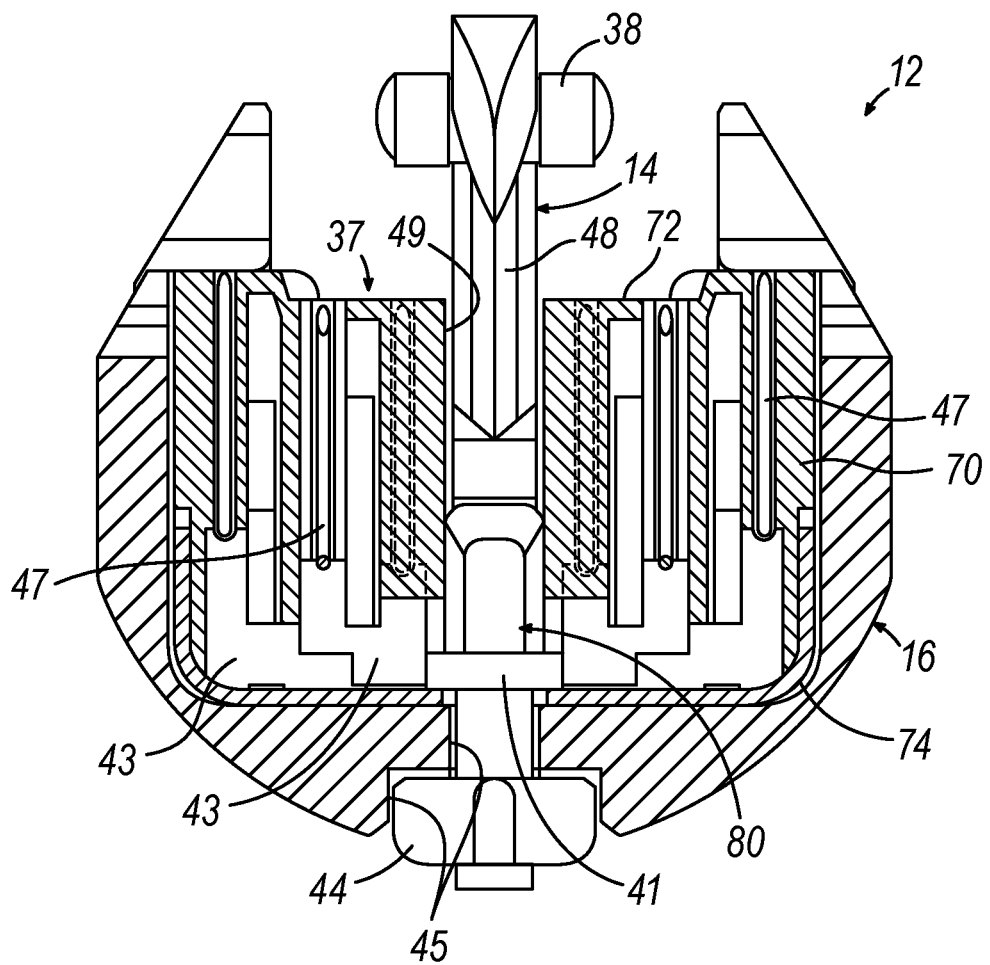
FIG. 5 depicts an end cross-sectional view of the end effector of FIG. 3, taken along line 5-5 of FIG. 3.
Figure 6:
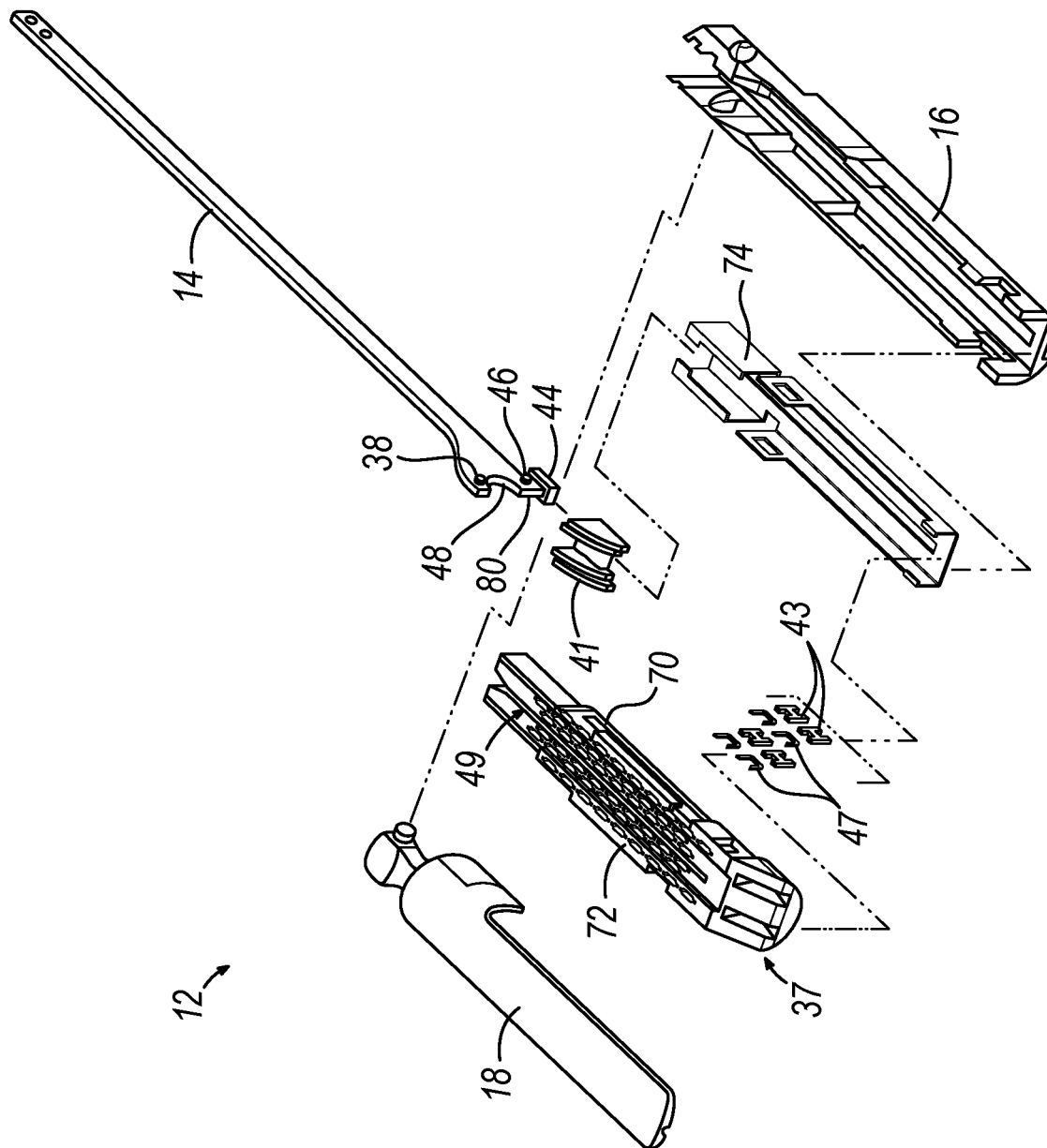
FIG. 6 depicts an exploded perspective view of the end effector of FIG. 3.

FIG. 3 shows firing beam (14) of the present example proximally positioned and anvil (18) pivoted to an open configuration, allowing an unspent staple cartridge (37) to be removably installed into a channel of lower jaw (16). As best seen in FIGS. 5-6, staple cartridge (37) of the present example includes a cartridge body (70), which presents an upper deck (72) and is coupled with a lower cartridge tray (74). As best seen in FIG. 3, a vertical slot (49) extends longitudinally through a portion of staple cartridge body (70). As also best seen in FIG. 3, three rows of staple apertures (51) are formed through upper deck (72) on each lateral side of vertical slot (49). As shown in FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). Each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

With end effector (12) closed, as depicted in FIGS. 4A-4B by distally advancing closure tube (32) and closure ring (33), firing beam (14) is then advanced distally into engagement with anvil (18) by having upper pin (38) enter longitudinal anvil slot (42). A pusher block (80) (shown in FIG. 5) located at distal end of firing beam (14) pushes wedge sled (41) distally as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43), which in turn drives staples (47) out through staple apertures (51) and into forming contact with staple forming pockets (53) (shown in FIG. 3) on inner surface of anvil (18). FIG. 4B depicts firing beam (14) fully distally translated after completing severing and stapling of tissue. Staple forming pockets (53) are intentionally omitted from the view in FIGS. 4A-4B but are shown in FIG. 3. Anvil (18) is intentionally omitted from the view in FIG. 5.

Figure 7:
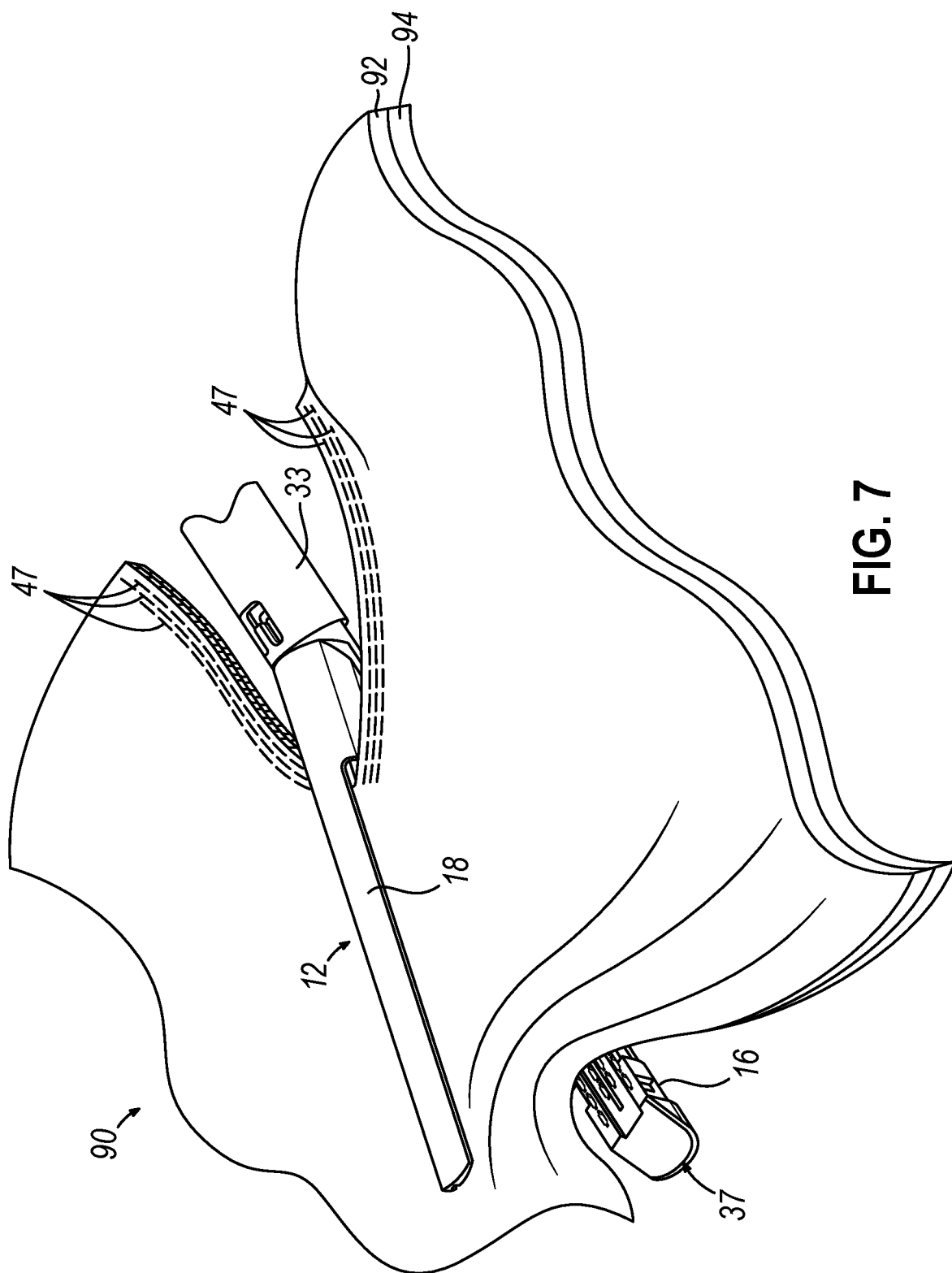
FIG. 7 depicts a perspective view of the end effector of FIG. 3, positioned at tissue and having been actuated once in the tissue.

FIG. 7 shows end effector (12) having been actuated through a single firing stroke through tissue (90). Cutting edge (48) (obscured in FIG. 7) has cut through tissue (90), while staple drivers (43) have driven three alternating rows of staples (47) through tissue (90) on each side of the cut line produced by cutting edge (48). After the first firing stroke is complete, end effector (12) is withdrawn from the patient, spent staple cartridge (37) is replaced with a new staple cartridge (37), and end effector (12) is then again inserted into the patient to reach the stapling site for further cutting and stapling. This process may be repeated until the desired quantity and pattern of firing strokes across the tissue (90) has been completed.

Instrument (10) may be further constructed and operable in accordance with any of the teachings of the following references, the disclosures of which are incorporated by reference herein: U.S. Pat. No. 8,210,411, entitled "Motor-Driven Surgical Instrument," issued Jul. 3, 2012; U.S. Pat. No. 9,186,142, entitled "Surgical Instrument End Effector Articulation Drive with Pinion and Opposing Racks," issued on Nov. 17, 2015; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; U.S. Pat. No. 9,717,497, entitled "Lockout Feature for Movable Cutting Member of Surgical Instrument," issued Aug. 1, 2017; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 9,839,421, entitled "Jaw Closure Feature for End Effector of Surgical Instrument," issued Dec. 12, 2017; and/or U.S. Pat. No. 10,092,292, entitled "Staple Forming Features for Surgical Stapling Instrument," issued Oct. 9, 2018.

II. Exemplary Buttress Assembly and Buttress Applier Cartridge

In some instances, it may be desirable to equip end effector (12) of surgical instrument (10) with an adjunct material, such as a buttress, to reinforce the mechanical fastening of tissue provided by staples (47). Such a buttress may prevent the applied staples (47) from pulling through the tissue and may otherwise reduce a risk of tissue tearing at or near the site of applied staples (47). In addition to or as an alternative to providing structural support and integrity to a line of staples (47), a buttress may provide various other kinds of effects such as spacing or gap-filling, administration of therapeutic agents, and/or other effects. In some instances, a buttress may be provided on upper deck (72) of staple cartridge (37). As described above, deck (72) houses staples (47), which are driven by staple driver (43). In some other instances, a buttress may be provided on the surface of anvil (18) that faces staple cartridge (37). It should also be understood that a first buttress may be provided on upper deck (72) of staple cartridge (37) while a second buttress is provided on anvil (18) of the same end effector (12).

Various examples of forms that a buttress may take will be described in greater detail below. Various ways in which a buttress may be secured to a staple cartridge (37) or an anvil (18) will also be described in greater detail below. Exemplary buttress assemblies, exemplary materials and techniques for applying buttress assemblies, and exemplary buttress applier cartridges may be configured in accordance with at least some of the teachings of U.S. Pat. No. 10,166,023, entitled "Method of Applying a Buttress to a Surgical Stapler End Effector," issued Jan. 1, 2019; and/or in U.S. Pat. No. 10,349,939, entitled "Method of Applying a Buttress to a Surgical Stapler," issued Jul. 16, 2019, the disclosures of which are incorporated by reference herein.

A. Exemplary Composition of Buttress Assembly

Figure 8:
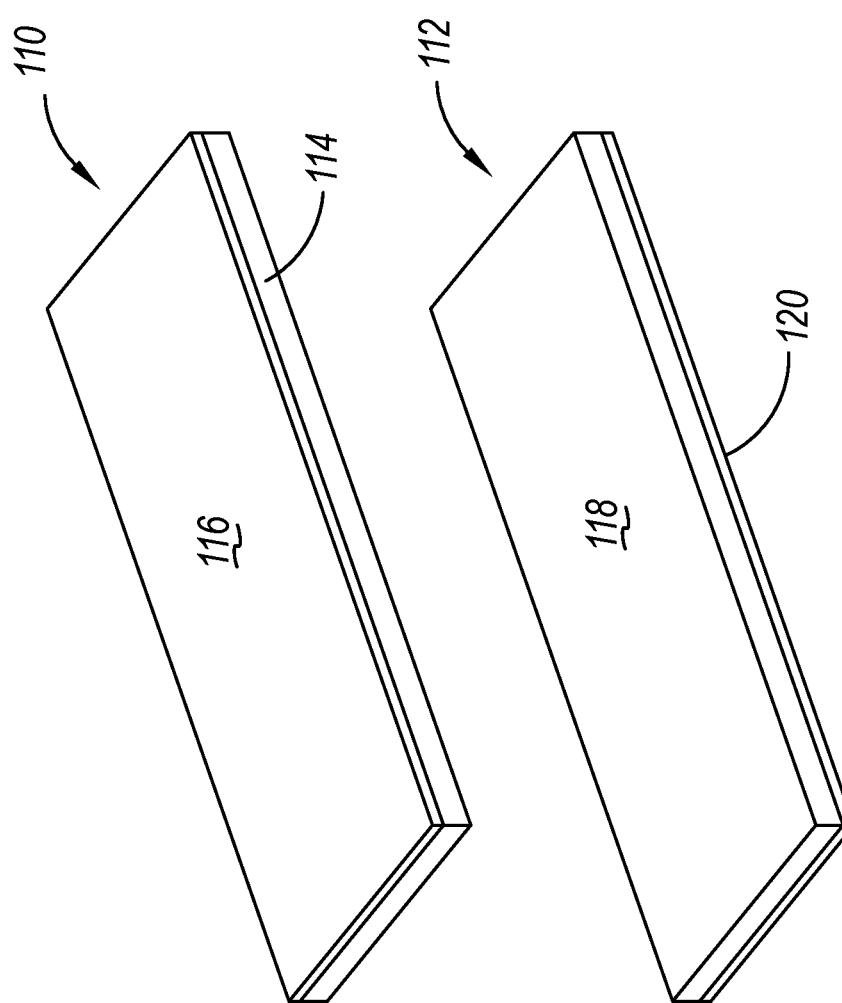
FIG. 8 depicts a perspective view of an exemplary pair of buttress assemblies, each of which may be applied to a jaw of the end effector of FIG. 3.

FIG. 8 shows an exemplary pair of buttress assemblies (110, 112) (each also referred to individually as a "buttress"). Buttress assembly (110) of this example comprises a buttress body (114) and an upper adhesive layer (116). Similarly, buttress assembly (112) comprises a buttress body (118) and a lower adhesive layer (120). In the present example, each buttress body (114, 118) comprises a strong yet flexible material configured to structurally support a line of staples (47). By way of example only, each buttress body (114, 118) may comprise a mesh of polyglactin 910 material by Ethicon, Inc. of Somerville, N.J. Alternatively, any other suitable materials or combinations of materials may be used in addition to or as an alternative to polyglactin 910 material to form each buttress body (114, 118).

Each buttress body (114, 118) may comprise a material including, for example, a hemostatic agent such as fibrin to assist in coagulating blood and reduce bleeding at the severed and/or stapled surgical site along tissue ($T_1$, $T_2$). As another merely illustrative example, each buttress body (114, 118) may comprise other adjuncts or hemostatic agents such as thrombin may be used such that each buttress body (114, 118) may assist to coagulate blood and reduce the amount of bleeding at the surgical site. Other adjuncts or reagents that may be incorporated into each buttress body (114, 118) may further include but are not limited to medical fluid or matrix components.

In the present example, adhesive layer (116) is provided on buttress body (114) to adhere buttress body (114) to underside (124) of anvil (18). Similarly, adhesive layer (120) is provided on buttress body (118) to adhere buttress body (118) to upper deck (72) of staple cartridge (37). Such an adhesive material may provide proper positioning of buttress body (114, 118) before and during actuation of end effector (12); then allow buttress body (114, 118) to separate from end effector (12) after end effector (12) has been actuated, without causing damage to buttress body (114, 118) that is substantial enough to compromise the proper subsequent functioning of buttress body (114, 118).

B. Exemplary Stapling of Tissue with Buttress Assemblies

Figure 9:
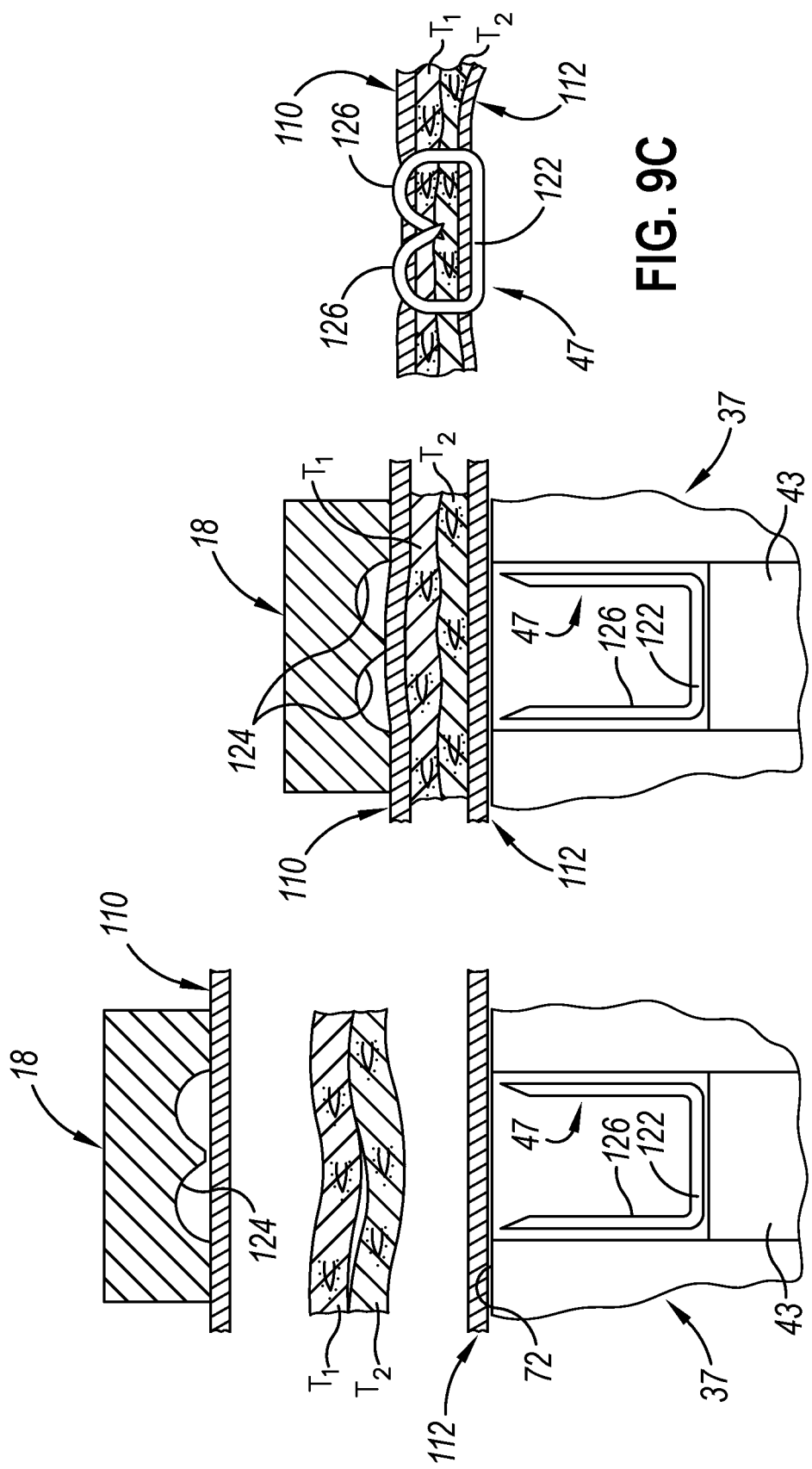
FIG. 9A depicts a cross-sectional end view of a portion of the end effector of FIG. 3 with the buttress assemblies of FIG. 8 applied to the upper and lower jaws of the end effector, showing the end effector jaws in an open state with tissue positioned between the upper and lower jaws.
FIG. 9B depicts a cross-sectional end view of the end effector and buttress assemblies of FIG. 9A, showing the end effector jaws in a closed state on the tissue.
FIG. 9C depicts a cross-sectional view of a formed staple and the buttress assemblies of FIG. 9A after having been secured to the tissue by the end effector of FIG. 3.

FIGS. 9A-9C show an exemplary sequence in which end effector (12), which has been loaded with buttress assemblies (110, 112), is actuated to drive staples (47) through two opposed layers of tissue ($T_1$, $T_2$), with buttress assemblies (110, 112) being secured to the same layers of tissue ($T_1$, $T_2$) by staples (47). In particular, FIG. 9A shows layers of tissue ($T_1$, $T_2$) positioned between anvil (18) and staple cartridge (37), with anvil (18) in open position. Buttress assembly (110) is adhered to underside (424) of anvil (18) via adhesive layer (116); while buttress assembly (112) is adhered to upper deck (72) of staple cartridge (37) via adhesive layer (120). Layers of tissue ($T_1$, $T_2$) are thus interposed between buttress assemblies (110, 112). Next, closure trigger (26) is pivoted toward pistol grip (24) to drive closure tube (32) and closure ring (33) distally. This drives anvil (18) to the closed position as shown in FIG. 9B. At this stage, layers of tissue ($T_1$, $T_2$) are compressed between anvil (18) and staple cartridge (37), with buttress assemblies (110, 112) engaging opposite surfaces of tissue layers ($T_1$, $T_2$). End effector (12) is then actuated as described above, driving staple (47) through buttress assemblies (110, 112) and tissue ($T_1$, $T_2$). As shown in FIG. 13C, crown (122) of driven staple (47) captures and retains buttress assembly (112) against layer of tissue ($T_2$). Deformed legs (126) of staple (47) capture and retain buttress assembly (110) against layer of tissue ($T_1$).

Figure 10:
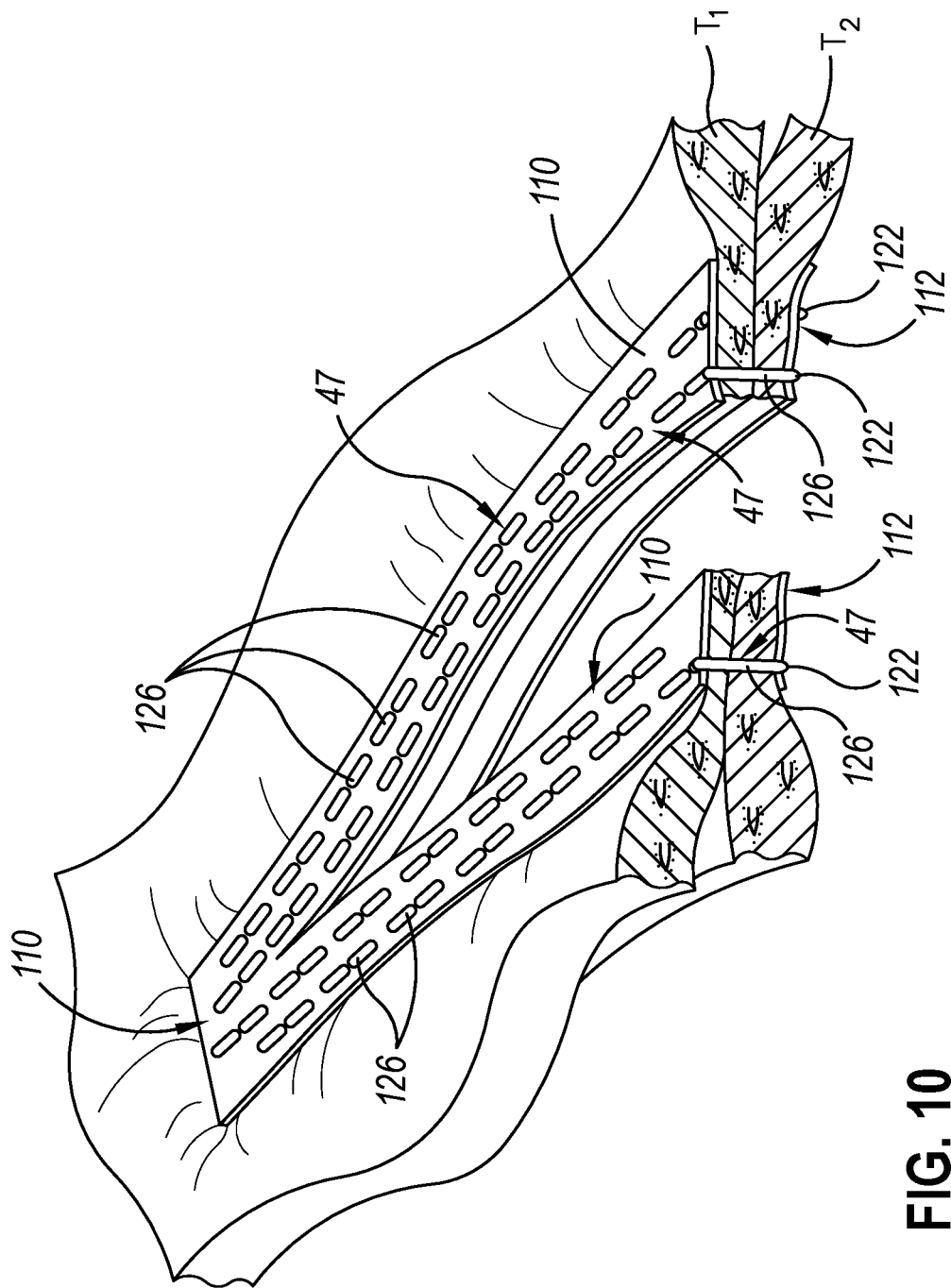
FIG. 10 depicts a perspective view of formed staples and the buttress assemblies of FIG. 9A after having been secured to the tissue by the end effector of FIG. 3.

A series of staples (47) similarly capture and retain buttress assemblies (110, 112) against layers of tissue ($T_1$, $T_2$), thereby securing buttress assemblies (110, 112) to tissue ($T_1$, $T_2$) as shown in FIG. 10. As end effector (12) is pulled away from tissue ($T_1$, $T_2$) after deploying staples (47) and buttress assemblies (110, 112), buttress assemblies (110, 112) disengage end effector such that buttress assemblies (110, 112) remain secured to tissue ($T_1$, $T_2$) with staples (47). Buttress assemblies (110, 112) thus provides structural reinforcement to the lines of staples (47) formed in tissue ($T_1$, $T_2$). As can also be seen in FIG. 10, distally presented cutting edge (48) of firing beam (14) also cuts through a centerline of buttress assemblies (110, 112), separating each buttress assembly (110, 112) into a corresponding pair of sections, such that each section remains secured to a respective severed region of tissue ($T_1$, $T_2$).

C. Exemplary Buttress Applier Cartridge with Active Retainer Arms

Figure 11:
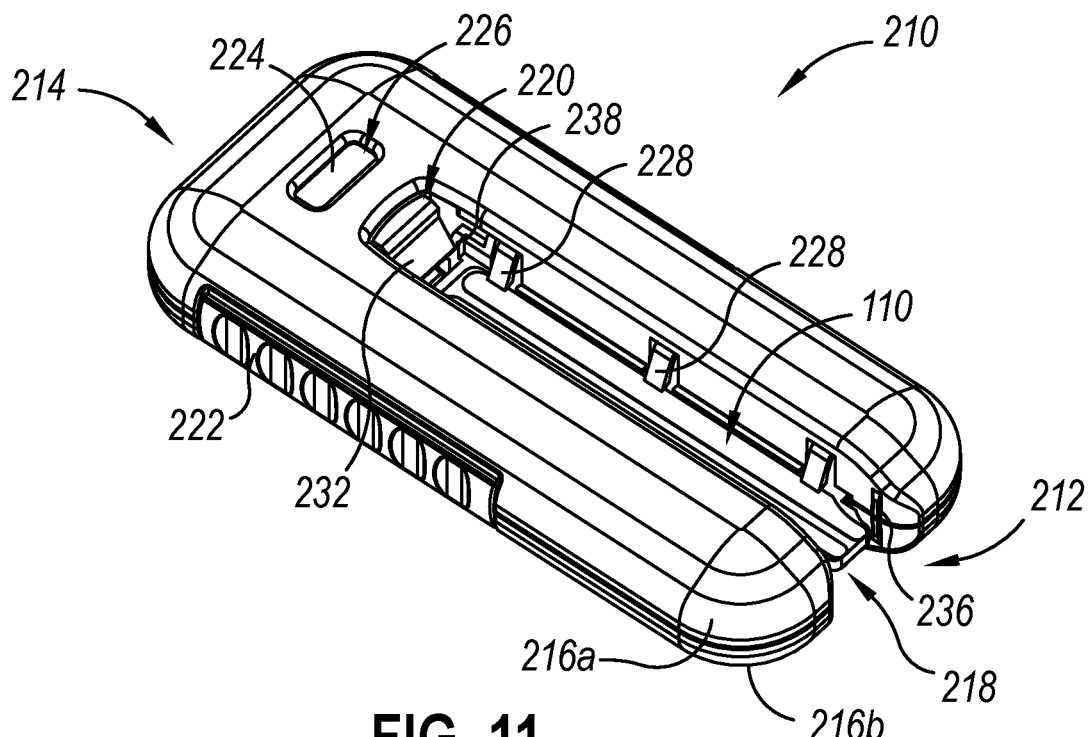
FIG. 11 depicts a perspective view of an exemplary buttress applier cartridge that may be used to carry and apply the buttress assemblies of FIG. 8.
Figure 12:
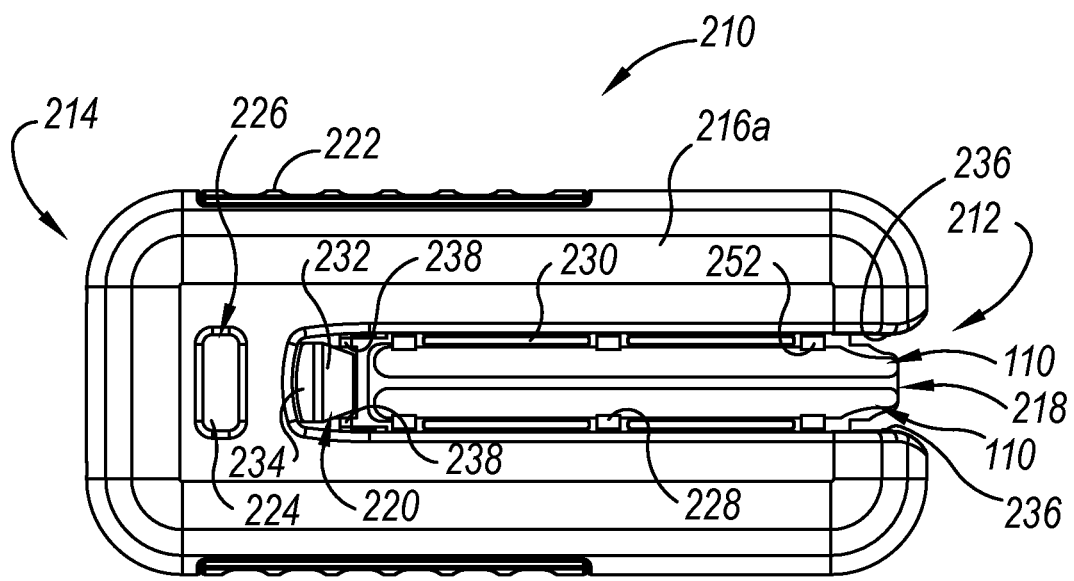
FIG. 12 depicts a top plan view of the buttress applier cartridge of FIG. 11.

Because end effector (12) of surgical instrument (10) may be actuated multiple times during a single surgical procedure, it may be desirable to enable an operator to repeatedly and easily load buttress assemblies (110, 112) onto lower jaw and anvil (16, 18) during that single surgical procedure. FIGS. 11-13B show an exemplary cartridge (210) (also referred to as a "buttress applicator") that may be used to support, protect, and apply adjunct material, such as buttress assemblies (110, 112), to end effector (12). As best seen in FIGS. 11-12, cartridge (210) of this example comprises an open end (212) and a closed end (214). Open end (212) is configured to receive end effector (12) as will be described in greater detail below. Cartridge (210) further includes a first housing (216a) and a second housing (216b), which each collectively generally define a "U" shape to present open end (212). A platform (218) and a sled retainer (220) are interposed between first and second housings (216a, 216b).

Platform (218) of the present example is configured to support a pair of buttress assemblies (110) on one side of platform (218) and another pair of buttress assemblies (112) on the other side of platform (218). Platform (218) is exposed in recesses that are formed between the prongs of the "U" configuration of first and second housings (216a, 216b). Each buttress assembly (110, 112) is provided in a respective pair of portions that are separated to avoid spanning across slots (42, 49) of anvil (18) and staple cartridge (37), respectively, though platform (218) may just as easily support wide versions of buttress assemblies (110, 112) that unitarily span across slots (42, 49) of anvil (18) and staple cartridge (37), respectively. More specifically, outer edges of platform (218) include retention features (530) in the form of ridges that further engage first and second housings (216a, 216b) to prevent platform (218) from sliding relative to first and second housings (216a, 216b).

First and second housings (216a, 216b) include integral gripping features (222) and indicator plates (224) positioned to correspond with windows (226) formed in first and second housings (216a, 216b), such that indicator plates (224) are visible through windows (226) at different times. Arms (228) of the present example are configured to selectively secure buttress assemblies (110, 112) to platform (218). In the present example, arms (228) are resilient and are thus configured to resiliently bear against buttress assemblies (110, 112), thereby pinching buttress assemblies (110, 112) against platform (218). Cartridge (210) includes a pair of tapered cam surfaces (232) and a respective pair of housing engagement features (234) positioned to engage corresponding surfaces of first and second housings (216a, 216b). First and second housings (216a, 216b) include proximal guide features (236) and distal guide features (238) configured to assist in providing proper alignment of end effector (40) with cartridge (210).

Figure 13A:
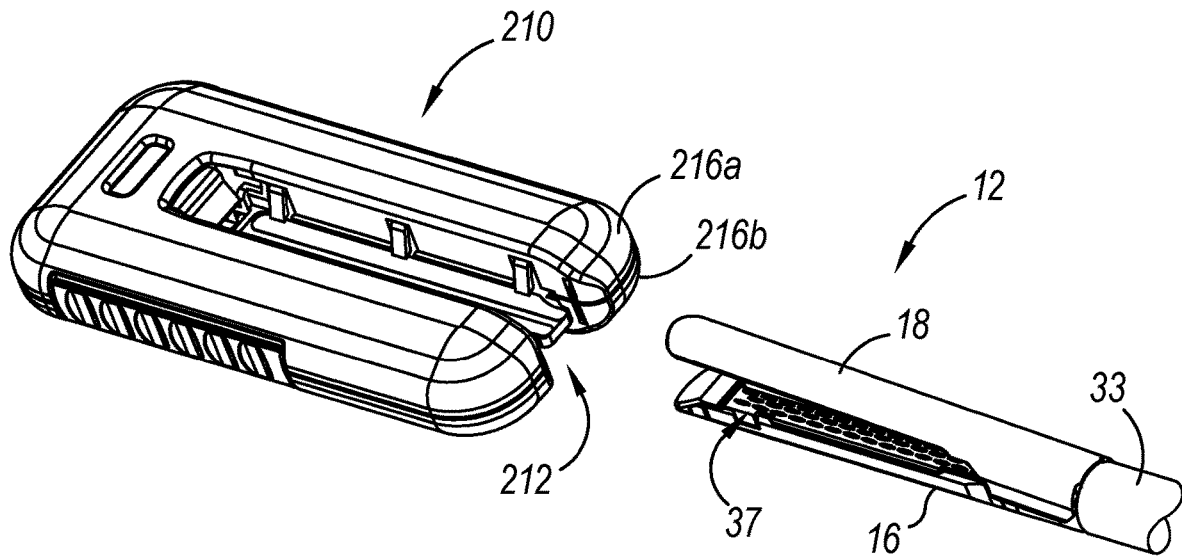
FIG. 13A depicts a perspective view of the end effector of FIG. 3 and the buttress applier cartridge of FIG. 11, showing the end effector and the buttress applier cartridge being aligned with one another.
Figure 13B:
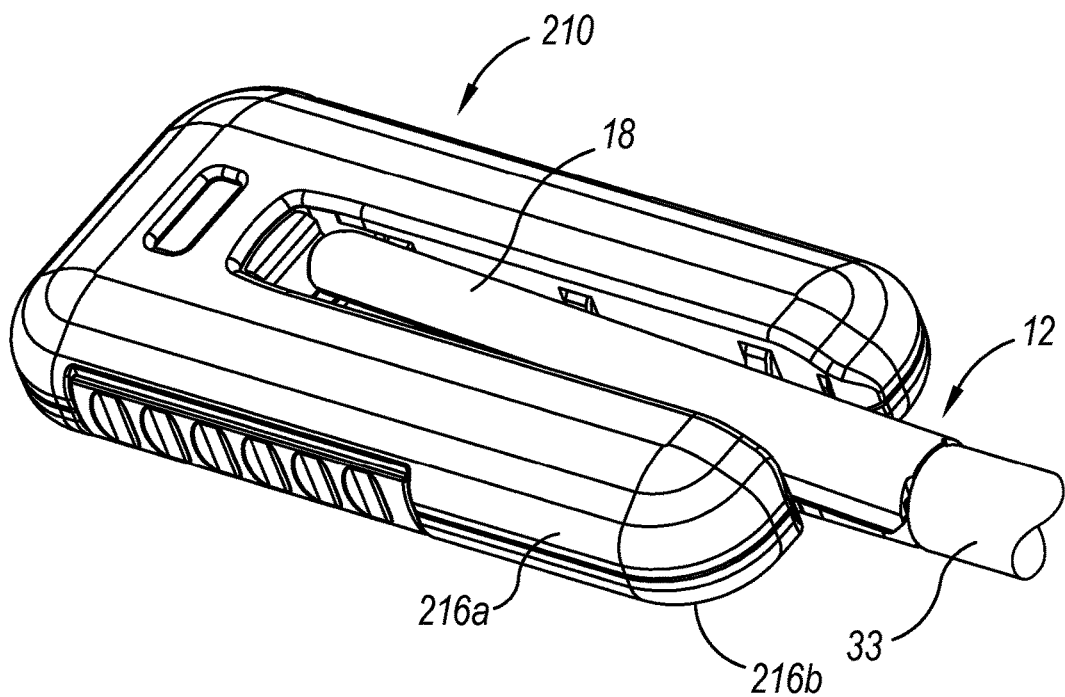
FIG. 13B depicts a perspective view of the end effector of FIG. 3 and the buttress applier cartridge of FIG. 11, with the end effectors jaws closed on a platform of the buttress applier cartridge.

FIG. 13A shows cartridge (210) in a configuration where retainer arms (228) are positioned to hold buttress assemblies (110, 112) against platform (218); while FIG. 13B shows cartridge (210) in a configuration where retainer arms (228) are positioned to release buttress assemblies (110, 112) from platform (218). While FIGS. 13A-13B only show buttress assembly (110) on platform (218), buttress assembly (112) would be retained on and released from platform (218) in an identical fashion. To use cartridge (210) to load end effector (12), the operator would first position cartridge (210) and end effector (12) such that end effector is aligned with open end (212) of cartridge (210) as shown in FIG.

13A. The operator would then advance end effector (12) distally, and/or advance cartridge (210) proximally, to position platform (218) and buttress assemblies (110, 112) between anvil (18) and staple cartridge (37) as shown in FIG. 13B. Closure trigger (26) of instrument (10) is then squeezed by the operator to close lower jaw and anvil (16, 18) on platform (218), thereby adhesively attaching buttress assemblies (110, 112) to anvil (18) and staple cartridge (37), and simultaneously depressing cam surface (232). Depression of cam surface (232) actuates retainer arms (228) laterally outwardly to thereby release buttress assemblies (110, 112) from platform (218), such that lower jaw and anvil (16, 18) may be disengaged from platform (218) while buttress assemblies (110, 112) remain adhered to anvil (18) and staple cartridge (37).

III. Exemplary Static Wedge Adjunct Applicator and Methods of Applying an Adjunct to a Surgical Stapler End Effector with Open Jaws In some instances, it may be desirable to provide an applicator device that is configured to apply a staple reinforcing adjunct element to one or both jaws of a surgical stapler end effector while the jaws remain in an open state, or otherwise without closing the jaws via actuation of the stapler's end effector closure system, such as via actuation of closure trigger (26) of surgical stapler (10). Exemplary applicator devices described below provide such functionality, such that each applicator device is configured to be manipulated relative to an end effector to apply an adjunct element to one or both jaws without requiring actuated closure of jaws like that shown in FIGS. 13A-13B described above.

It will be appreciated that any of the exemplary applicator devices described below may be configured to apply an adjunct element in the form of a buttress, such as buttress assemblies (110, 112) described above, or a tissue thickness compensator, for example of the type disclosed in U.S. Pat. Pub. No. 2012/0080336, entitled "Staple Cartridge Comprising Staples Positioned Within A Compressible Portion Thereof," published Apr. 5, 2012 and now abandoned, the disclosure of which is incorporated by reference herein. Additionally, application of a staple reinforcement element to an end effector jaw may be achieved with adhesive features as described above and/or with mechanical coupling features, for example of the type disclosed in U.S. Pat. No. 7,665,646, entitled "Interlocking Buttress Material Retention System," issued Feb. 23, 2010, the disclosure of which is incorporated by reference herein. Furthermore, any of the exemplary applicator devices described below may be suitably constructed for a single use or for multiple uses.

A. Exemplary Static Wedge Adjunct Applicator

In some instances, it may be desirable to provide a compact applicator configured to apply a staple reinforcing adjunct element to one or both jaws of a surgical stapler end effector while jaws remain in an open state, or otherwise without closing jaws via actuation of stapler's end effector closure system, such as via actuation of closure trigger (26) of surgical stapler (10).

Figure 14:
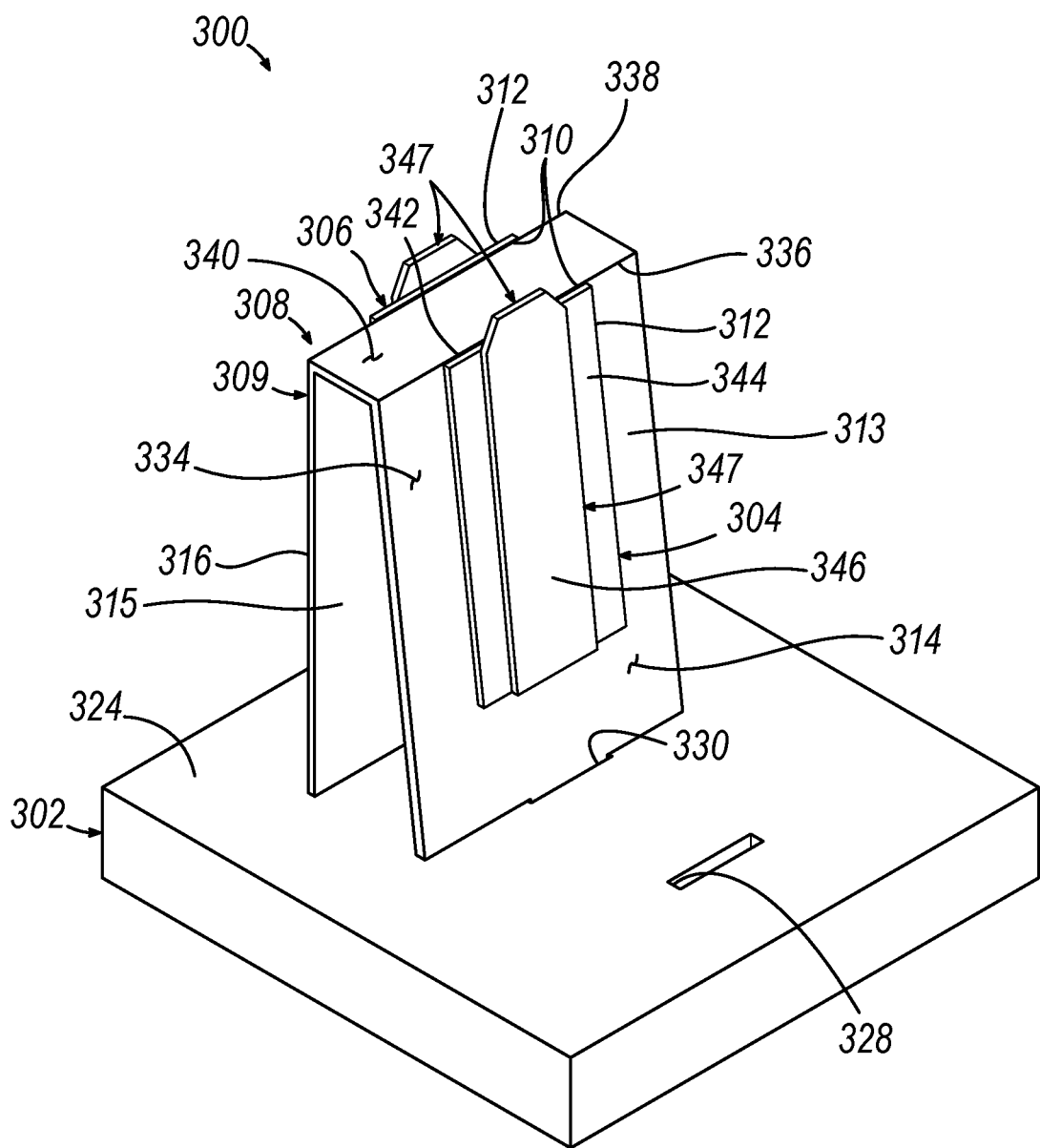
FIG. 14 depicts a perspective view of an exemplary adjunct applicator in a folded configuration and coupled with a base.
Figure 15:
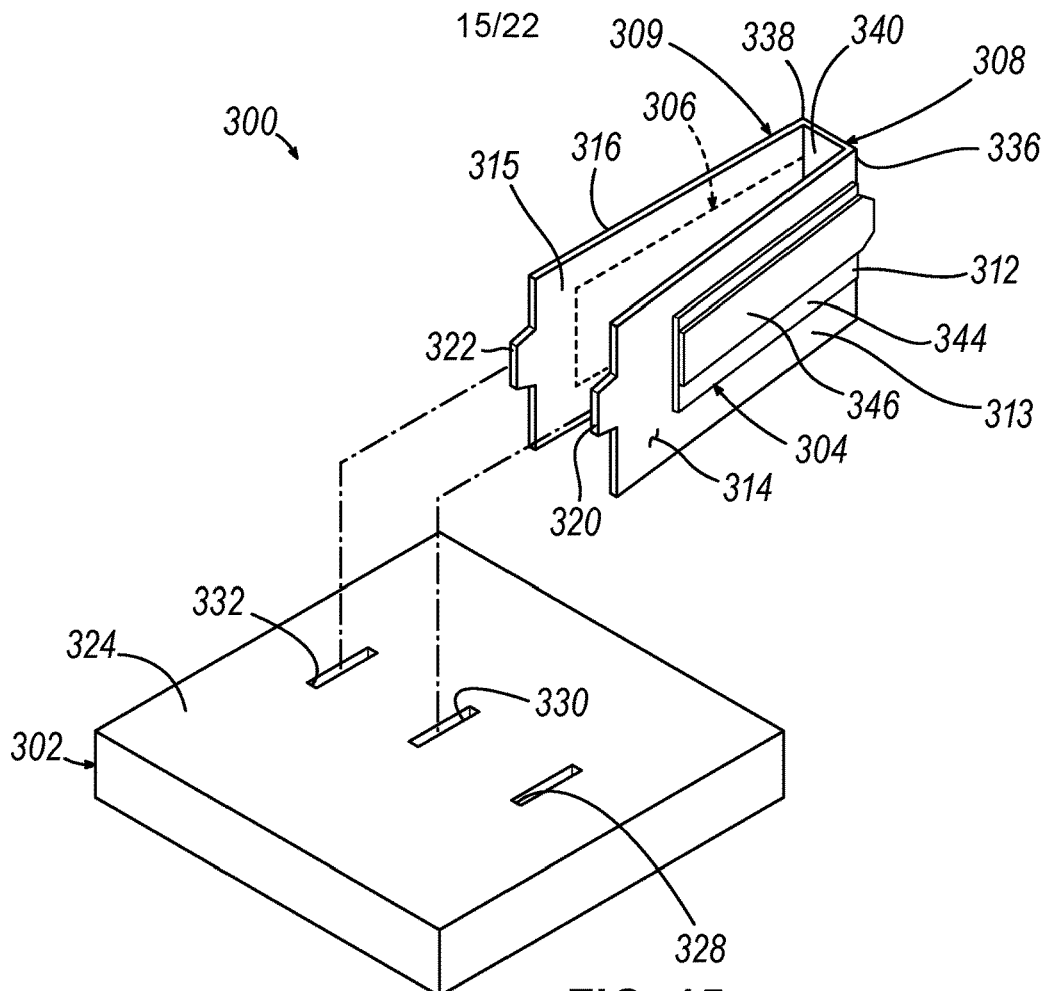
FIG. 15 depicts a perspective view of the adjunct applicator of FIG. 14 in the folded configuration and being positioned in relation to slots of the base.
Figure 16:
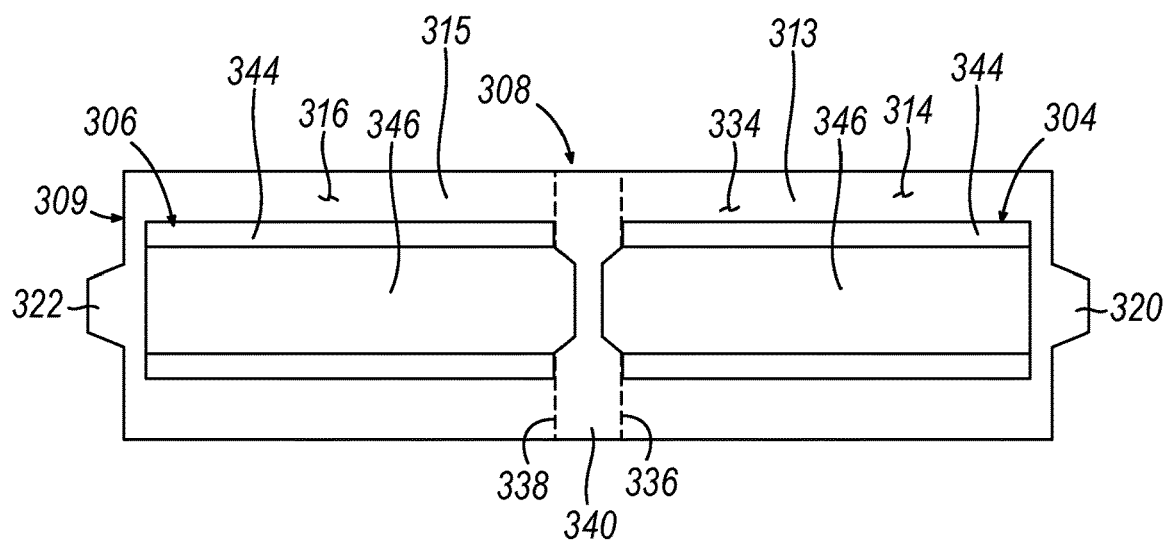
FIG. 16 depicts a plan view of the adjunct applicator of FIG. 14 in an unfolded configuration.

FIGS. 14-16 show an exemplary adjunct applicator assembly (300) including a wedge-shaped applicator member (308) and a base (302). Wedge-shaped applicator member (308) includes a body (309), a first adjunct element (304), and a second adjunct element (306). Body (309) may be disposable or reusable. In disposable versions, body (309) may be constructed of foamboard, cardboard, plastic or any other low-cost material known in the art that is sufficiently rigid, planar and provides support. Such versions of body (309) intended for disposal may be disposed of after a single use. In some versions, body (309) may be constructed of cardboard that may be treated with a surgically safe surface coating (334). Body (309) may include a corrugated or foam center with a rigid outer layer such as plastic or any other low-cost material known in the art to provide rigidity in a thin layer. In some reusable versions, body (309) may be constructed of a reusable material such as stainless steel or any other material known in the art to provide a sterilizable, sufficiently rigid surface that may be configured to assume different angles. In some versions, such reusable material may be pre-formed into the folded configuration and may be sterilized using a method described further below.

In the present example, body (309) of wedge-shaped applicator member (308) has a first body portion in the form of a first panel (313), a first body portion in the form of a second panel (315) opposed from the first panel (313), and a connecting panel (340) that joins a proximal end of first panel (313) with a proximal end of second panel (315). First panel (313) defines a first contact surface (314). First contact surface (314) is generally rectangular and lies on an exterior face of the first panel (313). The first panel (313) extends from connecting panel (340) to a first locating portion in the form of a first tang (320). First tang (320) has a trapezoidal shape having the wider base of the trapezoidal shape adjoined to the first panel (313) and the narrower top of the trapezoidal shape extending distally away from the first panel (313) from a central portion of the end opposite the connecting panel (340). Second panel (315) is also generally rectangular and defines a second contact surface (316) located on an exterior face opposite the second panel (315). Second panel (315) extends from connecting panel (340) to a second locating portion in the form of a second tang (322). Second tang (322) has a trapezoidal shape having the base adjoined to the second panel (315) and the top extending distally away from the second panel (315).

Each first and second adjunct element (304, 306) has a respective first side (310) and a respective second side (312). In the present version, first side (310) of each first and second adjunct element (304, 306) is configured to be releasably attached to first and second contact surfaces (314, 316), respectively, with a first attachment feature (342). First attachment feature (342) includes an adhesive (not shown) and/or a mechanical attachment such as retainer arms (228) (shown in FIG. 12), for example. First attachment feature (342) is configured to removably couple first and second adjunct elements (304, 306) to first and second contact surfaces (314, 316). In some versions, adhesive may be a glue, a cement, a mucilage, or a paste. In some versions, first attachment feature (342) may be of any type readily apparent to those of ordinary skill in the art to removably couple an adjunct to an applicator assembly in view of the teachings herein.

Second side (312) of each of first and second adjunct elements (304, 306) includes a second attachment feature (344) configured to attach to the open lower jaw and anvil (16, 18) of the end effector (12). Second attachment feature (344) has stronger bonding properties than first attachment feature (342). Second attachment feature (344) may also include a bonding agent (not shown) and/or a second mechanical attachment feature (not shown) similar to first attachment feature (342). Any combination of adhesives or mechanical attachments may be used for first and second attachment features (342, 344) so long as second attachment feature (344) has stronger attachment properties than first attachment feature (342). First and second adjunct elements (304, 306) may be in the form of buttress assemblies, such as buttress assemblies (110, 112) described above; or alternatively a tissue thickness compensator (not shown). Second sides (312) of first and second adjunct elements (304, 306) may have a film (346) that covers and protects second attachment feature (344). Film (346) may include a grasping portion (347) that extends proximally when the wedge-shaped applicator member (308) is in the folded configuration so that a user may easily remove the film (346) without disturbing the attachment properties of the first and second adjunct elements (304, 306).

In some versions, first and second adjunct elements (304, 306) may be a buttress including a three-layer, polymer construction including a core layer sandwiched between two outer layers to be collectively strong yet flexible to support a line of staples. In the present example, core layer is a polyglactin 910 material, whereas each outer layer is a polydioxanone or para-dioxanone (PDO) film material. Adjunct elements (304, 306) of the present example is formed by laminating core layers between outer layers between outer layers under a predetermined time. Adjunct elements (304, 306) is further mechanically cut to size thereby inhibiting abrasive edges, such as burs and or delamination, that could damage sensitive tissues. It will be appreciated that alternative methods of cutting adjunct elements (304, 306) such as a laser cutting, or hot knife cutting may be similarly used.

Base (302) may be constructed of foam, cardboard, plastic, or any other low-cost material known in the art to protect items from damage during shipping and to provide other structure support. Base (302) is configured to be placed on a work surface so that side (324) faces upwards. Side (324) of base (302) includes a first slot, a second slot, and a third slot (328, 330, 332) configured to accept first and second tangs (320, 322). Slots (328, 330, 332) are spaced apart and aligned with one another along a centerline of side (324). Slots (328, 330, 332) run transversely relative to the centerline (not shown) and are sized to accept tangs (320, 322). In some versions, base (302) may include a recess (not shown) configured to accept adjunct applicator assembly (300) and first and second adjunct elements (304, 306) within base (302) to protect adjunct applicator assembly (300) and first and second adjunct elements (304, 306) during shipping.

FIG. 15 shows adjunct applicator assembly (300) after wedge-shaped applicator member (308) has been transitioned from an unfolded position (shown in FIG. 16) into a folded position and is aligned to be fitted to base (302). In the folded position, the transverse distance between the first panel (313) and the second panel (315) gradually increases in a distal direction away from the connecting panel (340), thus providing body (309) with a wedge-like shape that tapers in a proximal direction toward connecting panel (340). In order to transition adjunct applicator assembly (300) from an unfolded position into a folded position, connecting panel (340) is folded so that first panel (313) and second panel (315) define a first angle ($\theta 1$) therebetween, which may range from approximately 20 degrees to approximately 45 degrees, for example. As shown in FIG. 15, adjunct applicator assembly (300) is vertically aligned with base (302) by aligning first tang (320) with a first slot (328), and the second tang (322) with a second slot (330). In other versions, base (302) may include one or more additional slots configured to set first and second panels (313, 315) at a one or more additional angles ranging from approximately 20 degrees to approximately 45 degrees.

In yet other versions, base (302) may include one or more pairs of slots (not shown) similar to slots (328, 330, 332) that are equally spaced apart from each other about a central point (not shown) along a centerline on side (324) so that tangs (320, 322) may be inserted into a first pair of slots. When tangs (320, 322) are inserted into first pair of slots a first angle ($\theta 1$) is formed between a first and second panels (313, 315). The distance between first panel (313) and second panel (315) increases as the first and second panels (313, 315) extend distally away from connecting panel (340). A second pair of slots are further spaced from the first pair of slots about the central point so that the first panel (313) and second panel (315) define a larger second angle ($\theta 2$) when first and second tangs (320, 322) are inserted into the second pair of slots that are further spaced from each other relative to the first pair of slots.

FIG. 16 shows wedge-shaped applicator member (308) in a planar, unfolded configuration. In the unfolded position, wedge-shaped applicator member (308) lies flat and extends longitudinally from the first tang (320) to the first panel (313). First panel (313) further extends distally to the connecting panel (340). Second panel (315) extends from the connecting panel (340) to the second tang (322). Adjunct applicator assembly (300) is configured to be contained within a sealed sterile barrier of product packaging (not shown) during shipping and storage so that body (309), first and second adjunct elements (304, 306), and base (302) remain sterile. By way of example only, such product packaging may be of the type disclosed in U.S. Pat. Pub. No. 2020/0205825, entitled "Method of Applying Buttresses to Surgically Cut and Stapled Sites," published Jul. 2, 2020, the disclosure of which is incorporated by reference herein. In order to house these components within a sterile barrier, it may be advantageous to minimize the size of adjunct applicator assembly (300) or otherwise provide adjunct applicator assembly (300) with the ability to be assembled from a collapsed state. It also may be advantageous to have base (302) function as a portion of the packaging material to protect adjunct applicator assembly (300) during shipping.

Connecting panel (340) of the present example is constructed as a joint or hinge that facilitates folding of the wedge-shaped applicator member (308). Connecting panel (340) is flat in the unfolded position and extends from a first crease (336) to a second crease (338). First crease (336) adjoins first panel (313) and second crease (338) adjoins second panel (315). First and second creases (336, 338) include a perforated or relieved portion that is transverse to a length of the wedge-shaped applicator member (308) The perforated or relieved portion is configured to facilitate flexing of connecting panel (340) relative to each of first panel (313) and second panel (315). As another merely illustrative example, connecting panel (340) may include only a first crease (336) or may include multiple creases and multiple end panels that are used to join first panel (313) with second panel (315). In yet another merely illustrative example, body (309) may be shipped in a partially folded configuration. In the partially folded configuration, first crease (336) is folded to 180 degrees, and second crease (338) remains straight so that a back side of the first panel (313) is folded over and engages a back side of the second panel (315) to conserve longitudinal space within the sterile barrier.

Figure 17A:
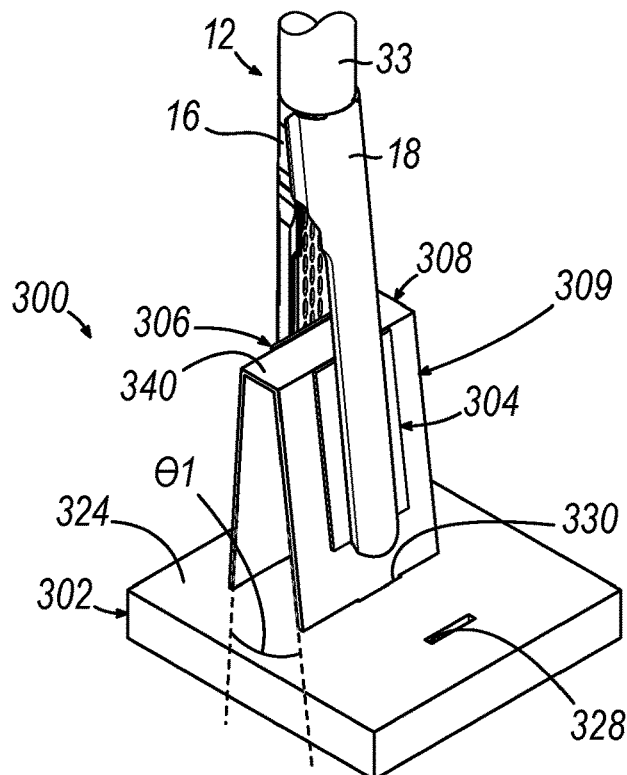
FIG. 17A depicts a perspective view of the jaws of the end effector of FIG. 3 in an open state and engaging the adjunct applicator of FIG. 14 while the applicator is in a first folded configuration defining a first angle.

FIG. 17A shows wedge-shaped applicator member (308) coupled to base (302) with the end effector (12) longitudinally aligned with the resulting adjunct applicator assembly (300). Base (302) is positioned on a work surface with side (324) facing upwardly such that slots (328, 330, 332) face upwardly. Wedge-shaped applicator member (308) is coupled to base (302) by inserting first tang (320) into first slot (328) and second tang (322) into second slot (330) and by pressing wedge-shaped applicator member (308) in a downward direction. First and second tangs (320, 322) coupled with first and second slots (330, 332) thereby fix the angular relationship between first and second panels (313, 315) to define a distally opening first angle (θ1). As described above, base (302) may include one or more additional slots configured so that the distally opening first angle (θ1) defined by first and second panels (313, 315) may be set to any desired angle.

Figure 17B:
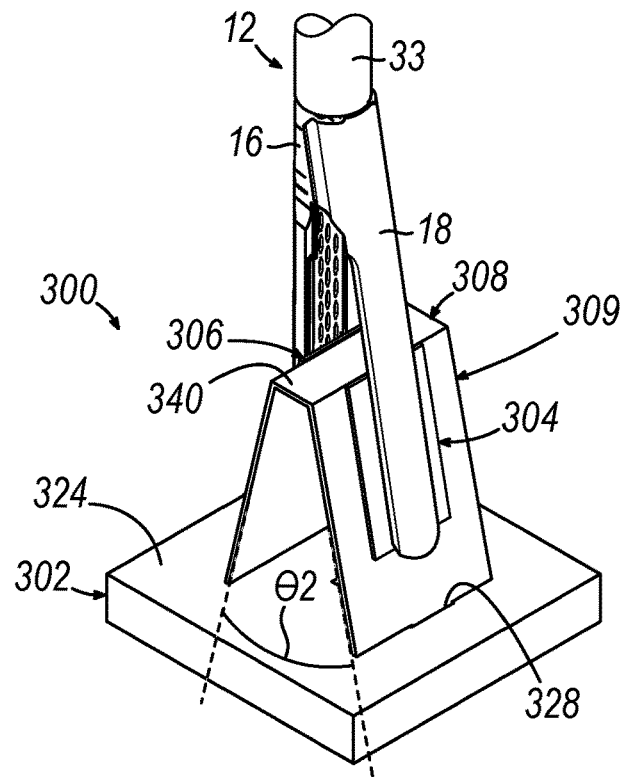
FIG. 17B depicts a perspective view of the jaws of the end effector of FIG. 3 in an open state and engaging the adjunct applicator of FIG. 14 while the applicator is in a second folded configuration defining a second angle, showing the applicator coupled with the base via a pair of slots.

FIG. 17B shows lower jaw and anvil (16, 18) of the end effector (12) in an open position engaging wedge-shaped applicator member (308) of adjunct applicator assembly (300). Film (346) has been removed from first and second adjunct elements (304, 306) before engaging adjunct applicator assembly (300) with lower jaw and anvil (16, 18) of the end effector (12). Lower jaw (16) of the end effector (12) engages second side (312) of first adjunct element (304) as anvil (18) simultaneously engages second side (312) of second adjunct element (306). Second attachment features (344), described above, of first and second adjunct elements (304, 306) attach to lower jaw and anvil (16, 18), respectively. While remaining in the open position, end effector (12) is then pulled upwardly away from adjunct applicator assembly (300). Second attachment features (344) of first and second adjunct elements (304, 306) remain attached to lower jaw and anvil (16, 18) as first attachment features (342) permit adjunct elements (304, 306) to release from first and second contact surfaces (314, 316) of wedge-shaped applicator member (308). First and second adjunct elements (304, 306) attached to lower jaw and anvil (16, 18) are ready to be used in a surgical procedure. It will be appreciated that by maintaining lower jaw and anvil (16, 18) in an open state while coupling adjunct elements (304, 306) to lower jaw and anvil (16, 18) with adjunct applicator assembly (300), the operator may control the force with which adjunct elements (304, 306) are seated onto lower jaw and anvil (16, 18) by selectively advancing end effector (12) longitudinally toward adjunct applicator assembly (300), which may remain stationary as illustrated in the present example.

B. Exemplary Static Wedge Adjunct Applicator with Angular Wings

In some instances, it may be desirable to modify adjunct applicator assembly (300) described above to include additional structural support to provide additional rigidity to first and second panels (313, 315) to inhibit first and second panels (313, 315) from bowing inwardly or outwardly so that adjunct elements (304, 306) evenly adhere to lower jaw and anvil (16, 18). FIGS. 18-21 show a second exemplary adjunct applicator assembly (400) that has a pair of first and second angular wings (446, 448) that may provide such functional benefits.

Figure 18:
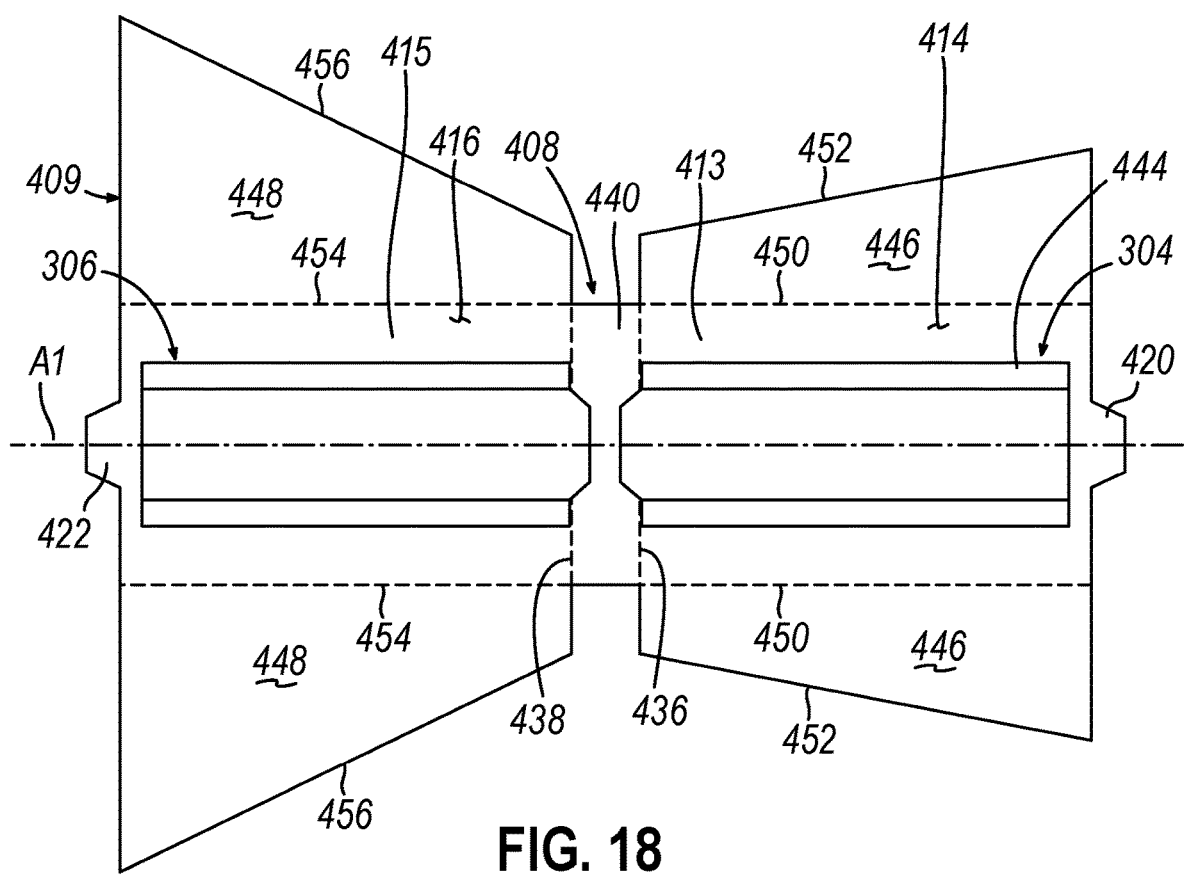
FIG. 18 depicts a plan view of a second exemplary adjunct applicator in an unfolded configuration.

FIG. 18 shows wedge-shaped applicator member (408) of adjunct applicator assembly (400) in an unfolded position. The adjunct applicator assembly (400) is constructed similarly to adjunct applicator assembly (300) described above, except as otherwise described below. The adjunct applicator assembly (400), like the adjunct applicator assembly (300), includes a wedge-shaped applicator member (408) and base (302). Wedge-shaped applicator member (408) includes a body (409) and first and second adjunct elements (304, 306). Wedge-shaped applicator member (408) and base (302) are constructed of similar materials as wedge-shaped applicator member (308) and base (302) of adjunct applicator assembly (300). As shown in FIG. 18, body (409) of adjunct applicator assembly (400) in an unfolded position extends longitudinally from a first tang (420) to a first panel (413). First panel (413) extends towards a connecting panel (440). Second panel (415) extends from the connecting panel (440) towards second tang (422). First and second panels (413, 415) define first and second contact surfaces (414, 416), respectively, similar to first and second contact surfaces (314, 316) of adjunct applicator assembly (300). First and second adjunct elements (304, 306) are attached on their first sides (310) to first and second contact surfaces (414, 416), respectively.

Body (409) of wedge-shaped applicator member (408) differs from body (309) of wedge-shaped applicator member (308) in that body (409) further includes first and second pair of angular wings (446, 448) formed on side portions of first and second panels (413, 415). In particular, a first pair of angular wings (446) is formed on the side portions of first panel (413) and are configured as trapezoidal shaped planar panels that extend transversely from first panel edges (450). First panel edges (450) run parallel to the length of unfolded body (409) along the outside edges of the first panel (413). First panel edges (450) may be perforated or relieved to facilitate bending or tearing of first angular wings (446) relative to first panel (413). In the present version, first pair of angular wings (446) forms a pair of trapezoidal planar panels. A right angle of the trapezoidal shape is located at the end proximate to first tang (420). First angular wings (446) each define a first outer edge (452) that is configured to abut an inside surface of second panel (415) to define a first predetermined angle (θ1) between first and second panels (413, 415) that opens distally and may range from approximately 20 degrees to approximately 45 degrees.

Second pair of angular wings (448) extend transversely from second panel edges (454) of second panel (415) to form trapezoidal planar panels each having a right angle. A right angle of each first angular wing (448) is located at the end proximate to first tang (420). Second panel edges (454) run parallel to the length of unfolded body (409) along an edge of second panel (415). Similar to first panel edges (450), second panel edges (454) may be perforated or relieved to facilitate bending of second pair of angular wings (448) relative to second panel (315) or tearing. Second pair of angular wings (448) is a mirror version of first pair of angular wings (446) and each second angular wing (448) defines a second outer edge (456) to define a second predetermined angle (θ2) (see FIG. 21) between first and second panels (413, 415) from approximately 20 degrees to approximately 45 degrees. Second angle (θ2) may be the same angle or a different angle from first angle (θ1).

Figure 19:
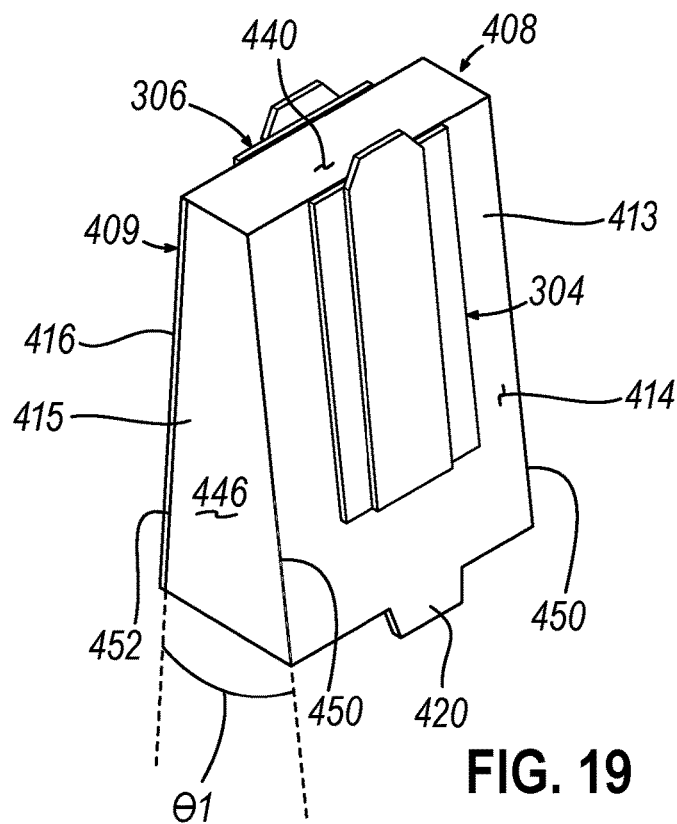
FIG. 19 depicts a perspective view of the adjunct applicator of FIG. 18 in a first folded configuration defining a first angle.
Figure 21:
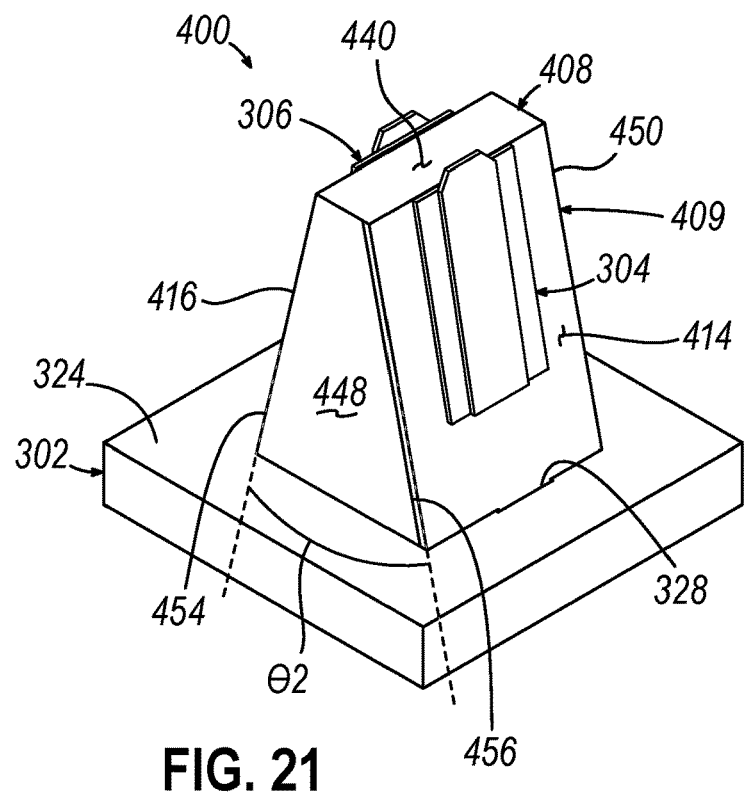
FIG. 21 depicts a perspective view of the adjunct applicator of FIG. 18 in a second folded configuration defining a second angle, showing the applicator coupled to the base via a pair of slots.

In the present example, second pair of angular wings (448) are suitably shaped such that the resulting second angle (θ2) is larger than the first angle (θ1) defined by first wings (446) between first and second panels (413, 415), for example as shown by FIG. 21 upon comparison with FIG. 19. Accordingly, a user may selectively deploy first wings (446) in the manner described above to define a relatively smaller first angle (θ1) between first and second panels (413, 415) for use with an end effector (12) having a relatively smaller jaw opening (also referred to as an "aperture") between the anvil (18) and the deck (72) of the staple cartridge (37) in the open state. Alternatively, the user may selectively deploy second pair of angular wings (448) in the manner described above to define a relatively larger second angle (θ2) between first and second panels (413, 415) for use with an end effector (12) having a relatively larger jaw opening in the open state.

FIG. 19 shows wedge-shaped applicator member (408) in a folded configuration after being transitioned from an unfolded configuration. Wedge-shaped applicator member (408) is transitioned into folded configuration by folding first and second panels (413, 415) relative to connecting panel (440) along first and second creases (436, 438). To transition wedge-shaped applicator member (408) from the unfolded configuration of FIG. 16 to one of the folded configurations shown in FIGS. 19 and 20, either first pair of angular wings (446) or second pair of angular wings (448) is folded along first or second panel edges (450, 454), respectively. First or second outer edges (452, 456) engage inside of the second panel (415) or first panel (413), respectively. For example, if the user desires to set adjunct applicator assembly (400) to first angle (θ1), the user may fold first pair of angular wings (446) inwards along first panel edges (450) to engage inside of the second panel (415). Second pair of angular wings (448) may be folded out of the way, remain unfolded, or be torn off along second panel edges (454) so that second pair of angular wings (448) do not interfere with first pair of angular wings (446) when first pair of angular wings (446) is folded to engage inside of first panel (413).

In order to set adjunct applicator assembly (400) to second angle (θ2), second pair of angular wings (448) are folded inwards along second panel edges (454) so that second outer edges (456) engages inner side of first panel (413). First pair of angular wings (446) may be folded out of the way, remain unfolded, or be torn along first panel edges (450) and discarded so that first pair of angular wings (446) do not interfere with second pair of angular wings (448) when second pair of angular wings (448) is folded to engage inside of the first panel (413).

Figure 20:
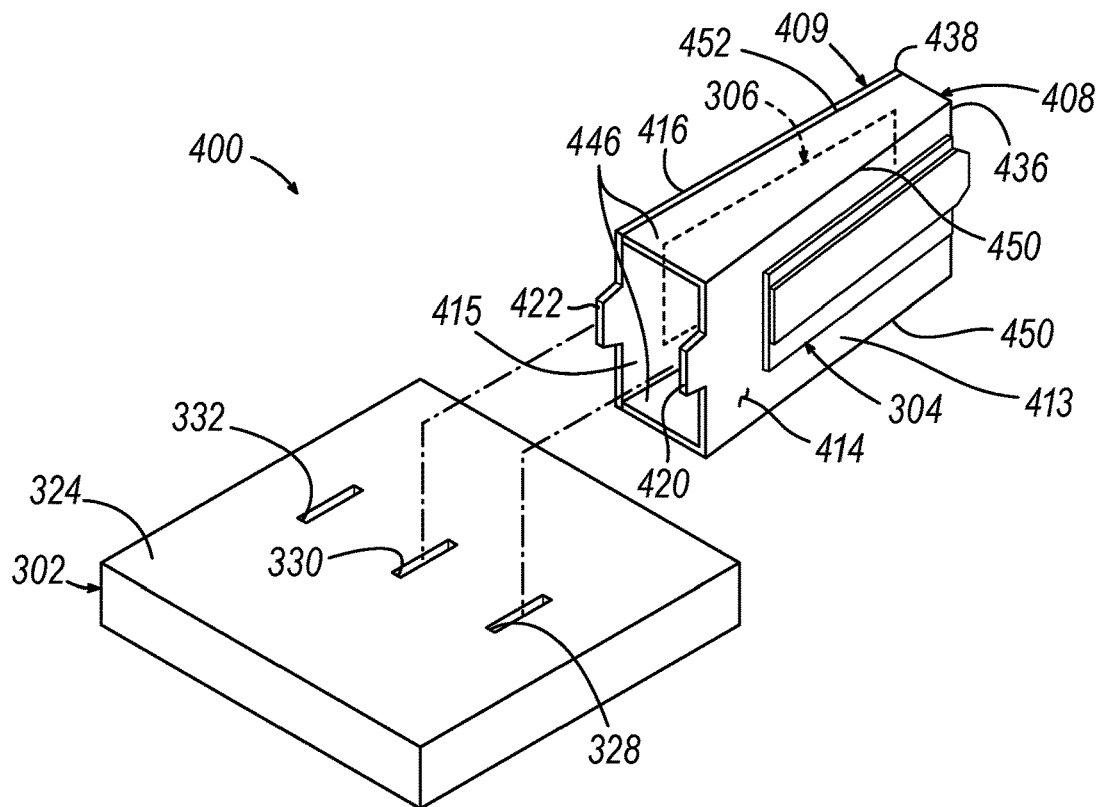
FIG. 20 depicts a perspective view of the adjunct applicator of FIG. 18 in the first folded configuration and being positioned in relation to a pair of slots of a base.

FIG. 20 shows adjunct applicator assembly (400) with wedge-shaped applicator member (408) in a first folded configuration in which first and second panels (413, 415) define first angle (θ1) therebetween, before wedge-shaped applicator member (408) is coupled to a base (302). Base (302) is placed on a work surface with side (324) facing upwardly. First slot (328) is longitudinally spaced from second slot (330) at a distance equal to the distance between first and second tangs (420, 422) when wedge-shaped applicator member (408) is set to first angle (θ1). First and second tangs (420, 422) are aligned with first and second slots (428, 430), and wedge-shaped applicator member (408) is then pressed downwardly, thereby inserting first and second tangs (420, 422) into first and second slots (428, 430).

FIG. 21 shows adjunct applicator assembly (400) with wedge-shaped applicator member (408) in a second folded configuration in which first and second panels (413, 415) define second angle (θ2) therebetween, and with wedge-shaped applicator member (408) coupled to base (302). First slot (328) in base (302) is spaced from third slot (332) at a distance equal to the distance between first and second tangs (420, 422) when the wedge-shaped applicator member (408) is set to second angle (θ2). Wedge-shaped applicator member (408) is coupled to base (302) by aligning first tang (420) with first slot (328) and inserting first tang (420) into first slot (328), while aligning second tang (422) with third slot (332), and inserting second tang (422) into third slot (332) by pressing wedge-shaped applicator member (408) in a downwards direction.

As described above, it will be appreciated that wedge-shaped applicator member (408) may be suitably configured to assume a variety of predetermined angular, wedge-shaped configurations, and slots (328, 330, 332) of base (302) may be suitably spaced from one another to receive tangs (420, 422) of wedge-shaped applicator member (408) in each of such predetermined configurations. Accordingly, a user may easily modify and adapt wedge-shaped applicator member (408) for use with end effectors (12) having jaw openings between the anvil (18) and the deck (72) of the staple cartridge (37) in the fully opened state.

C. Exemplary Static Wedge Adjunct Applicator with Adjustable Strut

Figure 24:
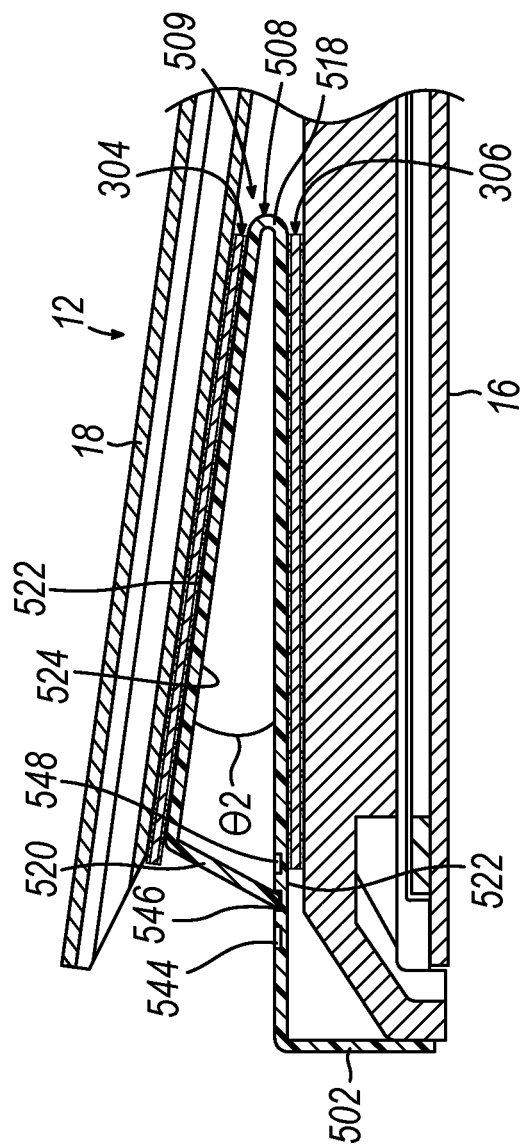
FIG. 24 depicts a side cross-sectional view of the end effector of FIG. 3 engaging the adjunct applicator of FIG. 22 while the applicator is in a second expanded, angular configuration.

In some instances, it may be desirable to attach adjuncts to open lower jaw and anvil (16, 18) of the end effector (12) with a compact, sterile, disposable adjunct applicator assembly. Additionally, it may be advantageous to set such an adjunct applicator assembly to different predetermined angles so that the adjunct applicator assembly may be used with different end effectors, and/or at optimal angles for particular adjuncts. It may also be desirable to have an adjunct applicator assembly that may be manipulated by the user to engage the open lower jaw and anvil (16, 18) of the end effector (12) without a base, such as base (302) described above, that requires a work surface. FIGS. 22-24 show a third exemplary adjunct applicator assembly (500) that may provide such functional benefits.

FIG. 22 shows adjunct applicator assembly (500) in a non-expanded, storage configuration. Adjunct applicator assembly (500) is similar to adjunct applicator assembly (300) described above, except as otherwise described below. Adjunct applicator assembly (500), like adjunct applicator assembly (300), includes a wedge-shaped applicator member (508), a first adjunct element (304), and a second adjunct element (306). Adjunct applicator assembly (500) is also configured to be contained within a sealed sterile barrier of product packaging (not shown) during shipping and storage so that sealed within a sterile bag (not shown) during shipping and storage. Adjunct applicator assembly (500) may be constructed of similar materials as adjunct applicator assembly (300). Adjunct applicator assembly (500) includes a body (509) that may be disposable or reusable. Adjunct applicator assembly (500) is configured to transfer first and second adjunct elements (304, 306) to open lower jaw and anvil (16, 18) of the end effector (12).

Adjunct applicator assembly (500) differs from adjunct applicator assembly (300) in that adjunct applicator assembly (500) is configured to be manipulated by hand and inserted into open lower jaw and anvil (16, 18) of end effector (12) without being coupled to base (302), and body (509) may be folded in a storage configuration to minimize the space that body (509) occupies within the sterile barrier of product packaging.

Body (509) includes a first panel (513), a second panel (515), a third panel (502), a first bending notch (504), a second bending notch (506), a connecting portion (518), and a strut (520). Body (509) extends proximally from third panel (502) to first bending notch (504) when in a non-expanded, storage position. Third panel (502) may serve as a handle configured to be ergonomically gripped by the user with a thumb and/or a finger. Third panel (502) is joined to first panel (513) at first bending notch (504). First bending notch (504) is a v-shaped notch located on an outside surface (522) of body (509) between third panel (502) and first panel (513). The outer surface (522) is an outwardly facing surface of the body (509). First bending notch (504) may include an adhesive (not shown) configured to retain third panel (502) in a transverse position relative to the longitudinally extending first panel (513) (shown in FIG. 23).

First panel (513) includes a first angle notch (544), a second angle notch (546), and a third angle notch (548) located on a distal portion of an inside surface (524). The inside surface (524) is an inwardly facing surface of the body (509). The first panel (513) extends proximally from the first bending notch (504) to connecting portion (518). Connecting portion (518) joins a proximal end of first panel (513) with a proximal end of second panel (515). Connecting portion (518) may be in the form of a flexible u-bend or a v-bend and is configured to enable first and second panels (513, 515) to angularly deflect relative to one another between a plurality of angular configurations. Connecting portion (518) may include one or more flexing features (538), which may be in the form of creases or interconnected panels (not shown) similar to first and second creases (336, 338) and connecting panel (340) of adjunct applicator assembly (300). Second panel (515) extends distally from connecting portion (518) to second bending notch (506). Second bending notch (506) is located on inside surface (554) at second panel (515) and joins strut (520) to second panel (515). Strut (520) extends distally from second bending notch (506) to strut end (540). Second bending notch (506) may be a v-shaped notch located on inside surface (554) of second panel (515). Strut end (540) is configured to selectively engage one of angle notches (544, 546, 548). First and second adjunct elements (304, 306) are releasably attached to the first and second panel (513, 515) on outside surface (522).

FIG. 23 shows adjunct applicator assembly (500) in a first expanded, angular configuration engaging open lower jaw and anvil (16, 18) of the end effector (12). Adjunct applicator assembly (500) has been transitioned from storage configuration (shown in FIG. 22) into the first angular configuration by bending both third panel (502) at first bending notch (504) and strut (520) at second bending notch (506). Third panel (502) is bent transversely downwards at first bending notch (504) relative to first panel (513) towards the outside surface (522). Strut (520) is bent transversely downwards at second bending notch (506) relative to second panel (515) towards inside surface (524) of first panel (513). In the illustrated example, strut end (540) engages first angle notch (544) and is retained by first angle notch (544). First angle notch (544) is distally located relative to second and third angle notches (546, 548). Strut end (540) is retained by first angle notch (544) so that first panel (513) and second panel (515) define a first angle (θ1) therebetween, which may range from approximately 20 degrees to approximately 45 degrees, for example. In the first folded position, the transverse distance between the first panel (513) and the second panel (515) gradually increases in a distal direction away from the connection portion (518), thus providing wedge-shaped applicator member (508) a wedge-like shape that tapers in a proximal direction toward connecting portion (518).

Film (346) is removed from second sides (312) of first and second adjunct elements (304, 306) before the lower jaw and anvil (16, 18) of end effector (12) engage the wedge-shaped applicator member (508). The user may grip or hold third panel (502) between a finger and a thumb of one hand while using the other hand to press the wedge-shaped applicator member (508) into the open lower jaw and anvil (16, 18) of the end effector (12). Open lower jaw and anvil (16, 18) of the end effector (12) will engage first and second adjunct elements (304, 306). Second sides (312) of first and second adjunct elements (304, 306) attach to open lower jaw and anvil (16, 18). The user then removes end effector (12) from wedge-shaped applicator member (508), which results in first and second adjunct elements (304, 306) detaching from applicator member (508) while remaining secured to open lower jaw and anvil (16, 18).

FIG. 24 shows adjunct applicator assembly (500) in a second expanded, angular position engaging and open lower jaw and anvil (16, 18) of the end effector (12). Wedge-shaped applicator member (508) has been transitioned from the storage position (shown in FIG. 22) into the second angular configuration in a manner similar to the first angular position (shown in FIG. 23) described above. In particular, third panel (502) is bent about first bending notch (504) and strut (520) is bent about second bending notch (506). Third panel (502) is bent transversely downwards relative to first panel (513) towards outside surface (522) at first bending notch (504). Strut (520) is bent transversely downwards at second bending notch (506) relative to second panel (515) towards inside surface (524) of first panel (513). Strut end (540) engages and is retained by second angle notch (546). Second angle notch (546) is proximal to first angle notch (544) and distal to third angle notch (548). Once strut end (540) is retained by second angle notch (546), first panel (513) and second panel (515) define a second angle (θ2) therebetween, which may range from approximately 20 degrees to approximately 45 degrees. In the present example, second angle (θ2) is greater than first angle (θ1) (shown in FIG. 23) in the second folded position, and thus the transverse distance between the first panel (513) and the second panel (515) gradually increases distally at a rate greater than in first folded position.

Though not shown, strut (520) may also be placed in third angle notch (548) so that first panel (513) and second panel (515) define a third angle between first panel (513) and second panel (515) that is greater than second angle (θ2) and which may be approximately 20 degrees to approximately 45 degrees. As another merely illustrative example, inside surface (524) of the first panel (513) may include one or more additional angle notches configured to define additional predetermined angles between first and second panels (513, 51) that range from approximately 20 degrees to approximately 45 degrees.

D. Exemplary Adjunct Applicator Assembly with Force Limiting Feature

Figure 25:
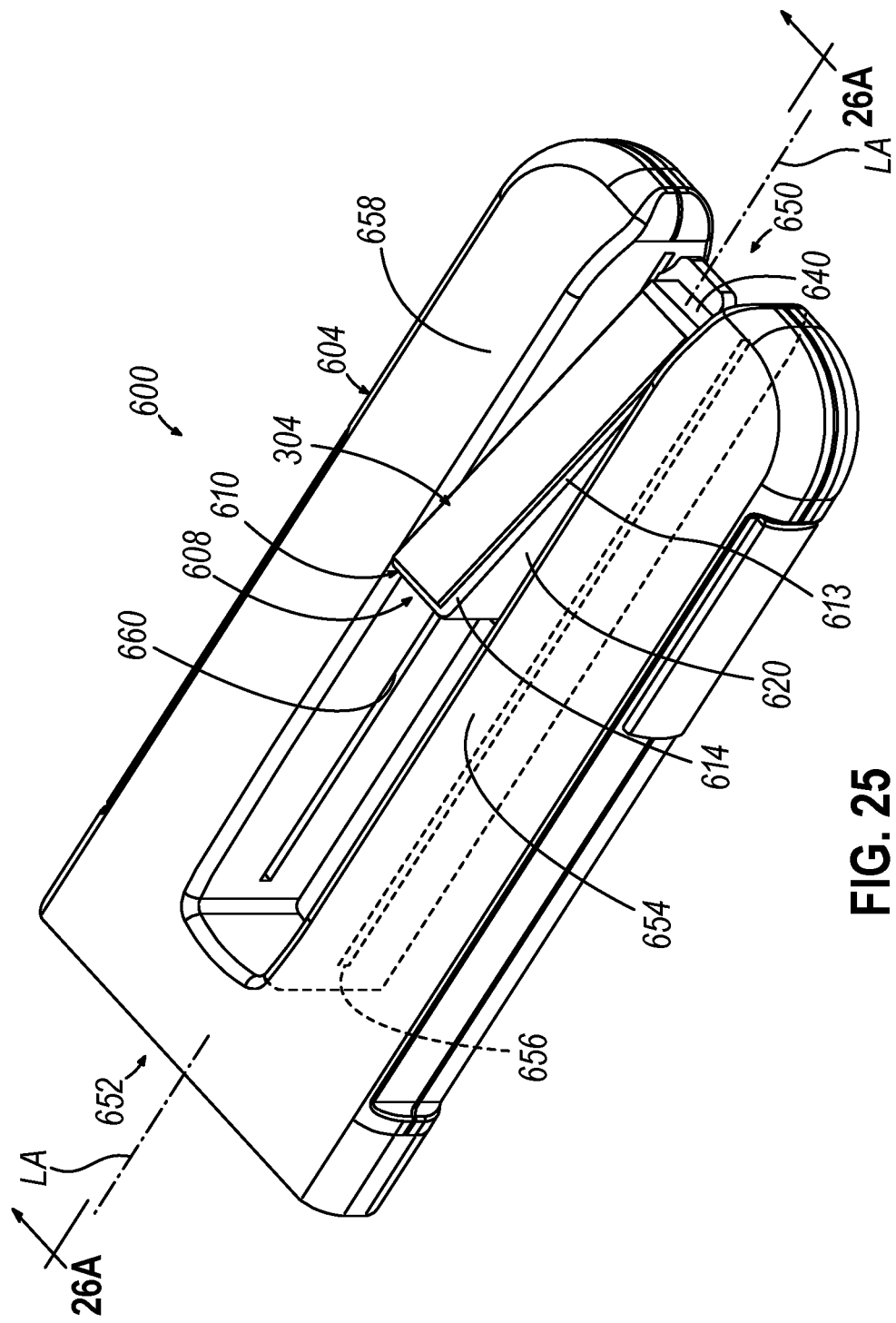
FIG. 25 depicts a perspective view of another exemplary adjunct applicator, showing a wedge portion of the applicator in a first longitudinal position.

In some instances, it may be desirable to limit the amount of force used to attach adjuncts to open lower jaw and anvil (16, 18) of end effector (12) to a predetermined amount of force to thereby avoid excessive application forces that might otherwise damage end effector (12) and/or adjunct elements (304, 306). FIGS. 25-26B show a fourth exemplary adjunct applicator assembly (600) that may provide such functional benefits.

As shown in FIG. 25, adjunct applicator assembly (600) includes a wedge-shaped applicator member (608), which may be similar in construction and function to any of the exemplary wedge-shaped applicator members (308, 408, 508) described above. Applicator member (608) includes a body (610) and first and second adjuncts (304, 306) disposed on opposing sides of body (610). Adjunct applicator assembly (600) further includes a resilient member in the form of a coil spring (602), a housing (604), and a linking feature (606). Housing (604) may be constructed similar to the combination of first and second housings (216A, 216B) of buttress applier cartridge (210) described above, and in the present example is configured as a chassis that provides a rigid support structure capable of supporting the wedge-shaped applicator member (608). The wedge-shaped applicator member (608) is slidably coupled to housing (604) by linking feature (606). Coil spring (602) biases body (610) proximally to a proximal position, shown in FIG. 26A. Body (610) may be constructed of a surgically safe plastic, stainless steel, or other material known in the art that is capable of being sterilized.

Similar to wedge-shaped applicator member (308) of adjunct applicator assembly (300), wedge-shaped applicator member (608) includes a first contact feature (613) that includes a first contact surface (614), a second contact feature (615) that includes a second contact surface (616), and a connecting feature (640) that interconnects first and second contact features (613, 615) at least at their proximal ends. First adjunct element (304) is mounted to first contact surface (614) of first contact feature (613), and second adjunct element (306) is mounted to second contact surface (616) of second contact feature (614). In some versions, connecting feature (640) may be suitably configured to enable first and second contact features (613, 615) to move toward and away from one another about their proximal ends through a range of angular positions in which body (610) defines a distally opening angle. In other versions, body (610) may be a static structure in which first and second contact features (613, 615) are angularly fixed relative to one another such that body (610) is configured to define a single distally opening angle.

Wedge-shaped applicator member (608) is slidably coupled to housing (604) with a plurality of support arms (642), and a movable member in the form of a roller (644). Each support arm (642) is fixedly attached to wedge-shaped applicator member (608) at a first end (646) and is rotatably coupled at a second end to roller (644). The present version includes up to four support arms (642), with two support arms (642) being attached to each lateral side of the wedge-shaped applicator member (608). Various other quantities and arrangements of support arms (642) may be employed in other versions. In yet other versions, movable member may be in the form of a slider, a puck, a ski, or any other structure known in the art that facilitates linear translation of a body relative to a chassis.

Housing (604) extends longitudinally from an open end (650) to a closed end (652) and has a "U" shape. Open end (650) is configured to receive open lower jaw and anvil (16, 18) of the end effector (12). Housing (604) further includes first and second housing side portions (654, 658) that extend longitudinally. First housing side portion (654) has a first channel (656) and second housing side portion (658) has a second channel (660) laterally opposed from first channel (656). First and second housing side portions (654, 658) collectively define the "U" shape of housing (604). Each channel (656, 660) houses one or more rollers (644). Each channel (656, 660) extends longitudinally along the respective first or second housing side portion (654, 658) and is configured to allow rollers (644) to rotate, thereby enabling wedge-shaped applicator member (608) to translate proximally and distally relative to housing (604).

Coil spring (602), shown in the form of an extension coil spring, is operatively attached between housing (604) and linking feature (606). In the present version, the linking feature (606) connects to a proximal portion of the wedge-shaped applicator member (608) within first housing side portion (654). In other versions, an additional coil spring (602) may be located within second housing side portion (658) and attached between additional linking feature (606) and a proximal portion of the housing (604). In yet other versions, linking feature (606) may be fitted between coil spring (602) and a distal portion of the housing (604). In all such versions, coil spring (602) is in a contracted, relaxed state when wedge-shaped applicator member (608) is in proximal position relative to housing (604).

FIG. 26A shows open lower jaw and anvil (16, 18) of the end effector (12) engaging first and second adjunct elements (304, 306) fitted to first and second contact surfaces (614, 616) with wedge-shaped applicator member (608) in the proximal position relative to housing (604), with the coil spring (602) in the contracted state. In proximal position, coil spring (602) biases wedge-shaped applicator member (608) in a proximal direction to proximal position. Open lower jaw and anvil (16, 18) of end effector (12) are forced distally against first and second adjunct elements (304, 306), which are supported by first and second contact features (613, 615), respectively.

FIG. 26B shows open lower jaw and anvil (16, 18) of end effector (12) being pressed distally with an amount of force that is sufficient to overcome the resilient bias of coil spring (602) and actuate wedge-shaped applicator member (608) from the proximal position (shown in FIG. 26A) to a distal position in which the coil spring (602) is extended. In order to transition applicator member (608) to the distal position, the user applies enough longitudinal input force to overcome the predetermined bias force that coil spring (602) proximally applies to wedge-shaped applicator member (608). Once the distal input force exerted by the user on applicator member (608) via end effector (12) overcomes the proximal bias force exerted on applicator member (608) by coil spring (602), wedge-shaped applicator member (608) moves distally relative to housing (604). This distal translatability of applicator member (608) relative to housing (604) and the resilient bias of extension coil spring (602) effectively limits the magnitude of force that end effector (12) can exert on applicator member (608) in response to a user input force. This configuration may ensure that the longitudinal compressive force mutually exerted between lower jaw and anvil (16, 18) and applicator member (608) is sufficient to effectively seat adjunct elements (304, 306) on lower jaw and anvil (16, 18), while also limiting such compressive force to protect lower jaw and anvil (16, 18) and applicator member (608) from damage due to otherwise excessive compression force.

Rollers (644) facilitate translation of wedge-shaped applicator member (608) distally and keep wedge-shaped applicator member (608) longitudinally aligned so that first and second adjunct elements (304, 306) are not misaligned while being applied to lower jaw and anvil (16, 18) of end effector (12). A portion of the end effector (12) may engage a stop feature of housing (604) to prevent coil spring (602) from being over-extended beyond a designed range of motion and applying more force than the predetermined amount of force to the first and second adjunct elements (304, 306). This allows the coil spring (602) to administer a predetermined amount of force proximally against lower jaw and anvil (16, 18) of the end effector (12). As described above, this predetermined force is enough force to attach second sides (312) of first and second adjunct elements (304, 306) to open lower jaw and anvil (16, 18) of end effector (12). Once a portion of end effector (12) engages the stop feature of housing (604), end effector (12) is moved proximally away from adjunct applicator assembly (600). The attachment force of second attachment feature (344) being greater than the attachment force of the first attachment feature (342) results in attachment of first and second adjunct elements (304, 306) to open lower jaw and anvil (16, 18) of the end effector (12).

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a body including: (i) a first body portion, (ii) a second body portion opposed from the first body portion, and (iii) a connecting portion that couples a proximal end of the first body portion with a proximal end of the second body portion, wherein the connecting portion is configured to permit the first and second body portions to move toward and away from one another between a plurality of angular orientations in each of which the body defines a distally opening angle; (b) a first adjunct element disposed on an outwardly facing surface of the first body portion; and (c) a second adjunct element disposed on an outwardly facing surface of the second body portion, wherein the first and second body portions are fixable relative to one another in each of the angular orientations such that the first body portion is configured to apply the first adjunct element to a first jaw of a surgical stapler end effector and the second body portion is configured to simultaneously apply the second adjunct element to a second jaw of the surgical stapler end effector.

Example 2

The apparatus of Example 1, wherein the distally opening angle defined by the body in the plurality of angular orientations ranges between approximately 20 degrees and approximately 45 degrees.

Example 3

The apparatus of any of the preceding Examples, further comprising a base removably coupled to the body, wherein the base is configured to support the body at the plurality of angular orientations.

Example 4

The apparatus of Example 3, wherein the body further includes a first tab extending from the first body portion and a second tab extending from the second body portion, wherein the first and second tabs are configured to mate with a plurality of slots in the base.

Example 5

The apparatus of any of the preceding Examples, further comprising a first pair of wings coupled to the first body portion, wherein the first pair of wings is configured to engage and support the second body portion relative to the first body portion to define and maintain the distally opening angle.

Example 6

The apparatus of Example 5, further comprising a second pair of wings coupled to the second body portion, wherein the second pair of wings is configured to engage the first body portion to define the distally opening angle.

Example 7

The apparatus of any of Examples 3 through 4, wherein the base includes a first slot configured to set the angular orientation of the body to define a first distally opening angle.

Example 8

The apparatus of Example 7, wherein the base includes a second slot configured to set the angular orientation of the body to define a second distally opening angle different than the first distally opening angle.

Example 9

The apparatus of any of the preceding Examples, wherein the first body portion includes a first panel and the second body portion includes a second panel.

Example 10

The apparatus of any of the preceding Examples, wherein at least one of the first or second adjunct elements include a buttress.

Example 11

The apparatus of any of the preceding Examples, wherein at least one of the first or second adjunct elements includes a tissue thickness compensator.

Example 12

The apparatus of any of the preceding Examples, wherein the first and second adjunct elements are releasably attached to the first and second body portions, respectively, with an adhesive.

Example 13

The apparatus of any of the preceding Examples, wherein the body includes a third body portion configured to be gripped by a user.

Example 14

The apparatus of any of the preceding Examples, further comprising a base having a first pair of slots and a second pair of slots, wherein the first pair of slots is configured to define a first distally opening angle of the body, wherein the second pair of slots is configured to define a second distally opening angle of the body.

Example 15

A surgical assembly comprising: (a) an end effector, wherein the end effector includes a first jaw having a plurality of staple forming pockets and a second jaw having a plurality of openings configured to house a plurality of staples; and (b) the apparatus of any of the preceding Examples, wherein the first body portion is configured to apply the first adjunct element to the first jaw, wherein the second body portion is configured to apply the second adjunct element to the second jaw.

Example 16

An assembly comprising: (a) a surgical stapler end effector including a first jaw and a second jaw; and (b) an adjunct applicator including: (i) a connection portion, (ii) a first body portion extending distally from the connection portion, (iii) a second body portion opposed from the first body portion and extending distally from the connection portion, wherein the first and second body portions are configured to define a distally opening angle, (iv) a first adjunct element positioned on the first body portion, and (v) a second adjunct element positioned on the second body portion, wherein the first body portion is configured to apply the first adjunct element to the first jaw and the second body portion is configured to apply the second adjunct element to the second jaw while the surgical stapler end effector is in an open state.

Example 17

The assembly of Example 16, wherein the apparatus further includes a strut hingedly coupled to the second body portion, wherein the first body portion includes one or more retaining notches arranged along a distal length of the first body portion, wherein the strut is configured to mate with a selected one of the retaining notches to define a corresponding distally opening angle between the first and second body portions.

Example 18

The assembly of any of Examples 16 through 17, wherein the apparatus further includes a third body portion hingedly connected to a distal end of the first body portion, wherein the third body portion is configured to deflect transversely relative to a longitudinal axis defined by a distal length of the first body portion, wherein the third body portion is configured to be gripped by a user.

Example 19

A method of applying an adjunct element to a jaw of a surgical instrument end effector with an applicator, wherein the applicator includes first and second body portions that are fixable relative to one another in a non-parallel arrangement such that the first and second body portions define a distally opening angle, wherein the adjunct element is positioned on one of the first or second body portions, the method comprising: (a) providing the end effector in an open position in which the end effector is configured to receive tissue between first and second jaws of the end effector; (b) positioning the end effector in the open position about the applicator such that the first jaw engages the first body portion and the second jaw simultaneously engages the second body portion; (c) moving the end effector and the applicator toward one another to apply the adjunct element to one of the first jaw or the second jaw; and (d) moving the end effector and the applicator apart from one another to separate the adjunct element from the applicator while the adjunct element remains attached to the one of the first jaw or the second jaw.

Example 20

The method of Example 19, further comprising moving the first body portion and the second body portion relative to one another to change the distally opening angle defined by the first body portion and the second body portion.

V. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. patent application Ser. No. 17/022,209 entitled "Apparatus and Method to Apply Buttress to End Effector of Surgical Stapler via Driven Member," filed on Sep. 16, 2020, issued as U.S. Pat. No. 11,564,683 on Jan. 31, 2023; U.S. patent application Ser. No. 17/022,414, entitled "Apparatus and Method to Apply Buttresses Separately to Jaws of End Effector of Surgical Stapler," filed on Sep. 16, 2020, issued as U.S. Pat. No. 11,452,523 on Sep. 27, 2022; U.S. patent application Ser. No. 17/022,414, entitled "Apparatus and Method to Close End Effector of Surgical Stapler onto Buttress," filed on Sep. 16, 2020, issued as U.S. Pat. No. 11,419,605 on Aug. 23, 2022; U.S. patent application Ser. No. 17/022,419, entitled "Apparatus and Method to Detect Full Seating of Buttress Applicator in End Effector of Surgical Stapler," filed on Sep. 16, 2020, issued as U.S. Pat. No. 11,559,306 on Jan. 24, 2023; U.S. patent application Ser. No. 17/022,422, entitled "Apparatus and Method to Apply Buttress to End Effector of Surgical Stapler with Authentication," filed on Sep. 16, 2020, issued as U.S. Pat. No. 11,413,040 on Aug. 16, 2022; and/or U.S. patent application Ser. No. 17/022,520, entitled "Method of Applying Buttress to End Effector of Surgical Stapler," filed on Sep. 16, 2020, issued as U.S. Pat. No. 11,660,093 on May 30, 2023. The disclosure of each of these U.S. patent applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An assembly comprising:
 (a) a surgical stapler end effector including a first jaw and a second jaw;
 (b) an adjunct applicator including:
 (i) a connection portion,
  (ii) a first body portion extending distally from the connection portion,
  (iii) a second body portion opposed from the first body portion and extending distally from the connection portion, wherein the first and second body portions are configured to define a distally opening angle,
  (iv) a first adjunct element positioned on the first body portion, and
  (v) a second adjunct element positioned on the second body portion; and
 (c) a strut moveably coupled to one of the first body portion or the second body portion, wherein the strut is configured to engage the other of the first body portion or the second body portion at a predefined location to define a distally opening angle between the first and second body portions, wherein the first body portion is configured to apply the first adjunct element to the first jaw and the second body portion is configured to apply the second adjunct element to the second jaw while the surgical stapler end effector is in an open state.

2. The assembly of claim 1, wherein the strut is hingedly coupled to the second body portion, wherein the first body portion includes one or more retaining notches arranged along a distal length of the first body portion, wherein the strut is configured to mate with a selected one of the retaining notches to define a corresponding distally opening angle between the first and second body portions.

3. The assembly of claim 1, wherein the assembly further includes a third body portion hingedly connected to a distal end of the first body portion, wherein the third body portion is configured to deflect transversely relative to a longitudinal axis defined by a distal length of the first body portion, wherein the third body portion is configured to be gripped by a user.

* * * * *